(12) United States Patent
Gamm et al.

(10) Patent No.: US 9,752,119 B2
(45) Date of Patent: Sep. 5, 2017

(54) SUBSTANTIALLY PURE HUMAN RETINAL PROGENITOR, FOREBRAIN PROGENITOR, AND RETINAL PIGMENT EPITHELIUM CELL CULTURES AND METHODS OF MAKING THE SAME

(71) Applicant: Wisconsin Alumni Research Foundation, Madison, WI (US)

(72) Inventors: David Matthew Gamm, Waunakee, WI (US); Jason Stephen Meyer, Indianapolis, IN (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/143,141

(22) Filed: Apr. 29, 2016

(65) Prior Publication Data
US 2016/0251618 A1    Sep. 1, 2016

Related U.S. Application Data

(62) Division of application No. 12/806,907, filed on Aug. 24, 2010, now Pat. No. 9,328,328.

(60) Provisional application No. 61/274,962, filed on Aug. 24, 2009.

(51) Int. Cl.
C12N 5/00 (2006.01)
C12N 5/079 (2010.01)
C12N 5/071 (2010.01)
A61K 35/30 (2015.01)

(52) U.S. Cl.
CPC ............ *C12N 5/0621* (2013.01); *A61K 35/30* (2013.01); *C12N 5/0602* (2013.01); *C12N 2501/11* (2013.01); *C12N 2501/115* (2013.01); *C12N 2501/16* (2013.01); *C12N 2501/91* (2013.01); *C12N 2506/02* (2013.01); *C12N 2506/45* (2013.01)

(58) Field of Classification Search
CPC .......................... C12N 5/0621; C12N 2501/16
See application file for complete search history.

(56) References Cited

PUBLICATIONS

Gamm et al. Stem Cells 26(12):3182-3193, 2008.*
Meyer et al. Stem Cells 29(8):1206-1218, 2011.*

* cited by examiner

*Primary Examiner* — Marcia S Noble
(74) *Attorney, Agent, or Firm* — Quarles & Brady LLP

(57) ABSTRACT

Methods for producing substantially pure cultures of human neural retinal progenitor cells, forebrain progenitor cells, and retinal pigment epithelial cells are disclosed. In addition, the successful differentiation of human embryonic stem cells and human induced pluripotent stem cells through the major developmental stages of human retinogenesis is disclosed.

11 Claims, 33 Drawing Sheets
(29 of 33 Drawing Sheet(s) Filed in Color)

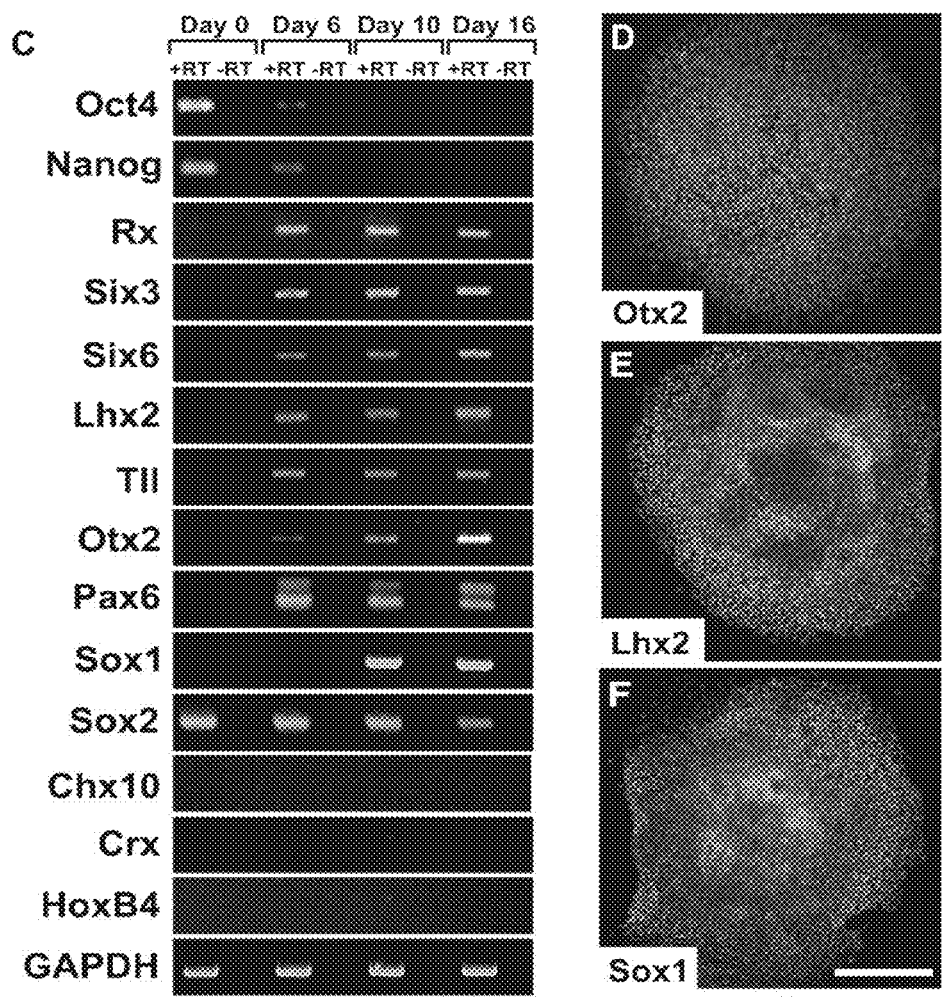
FIGS. 1A-1F, continued

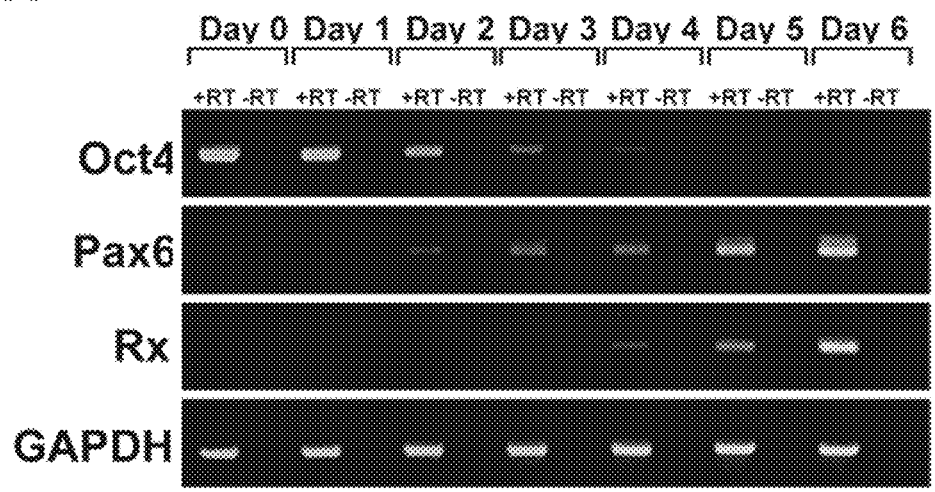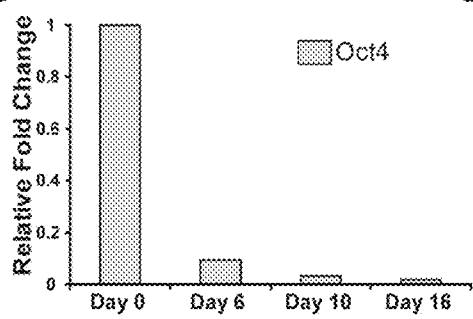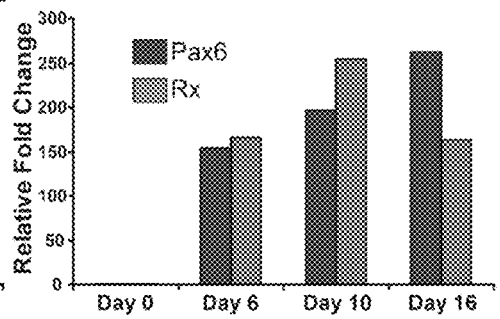
FIGS. 2A-2I

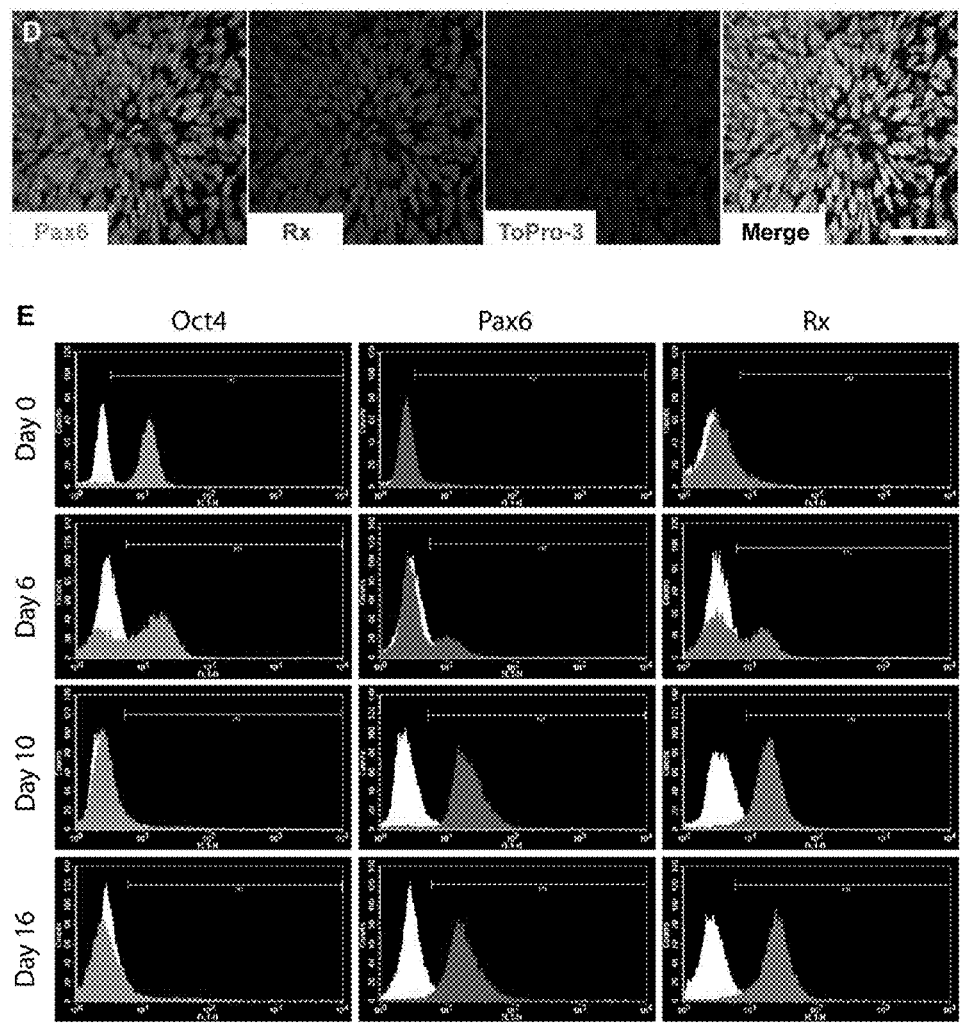
FIGS. 2A-2I, continued

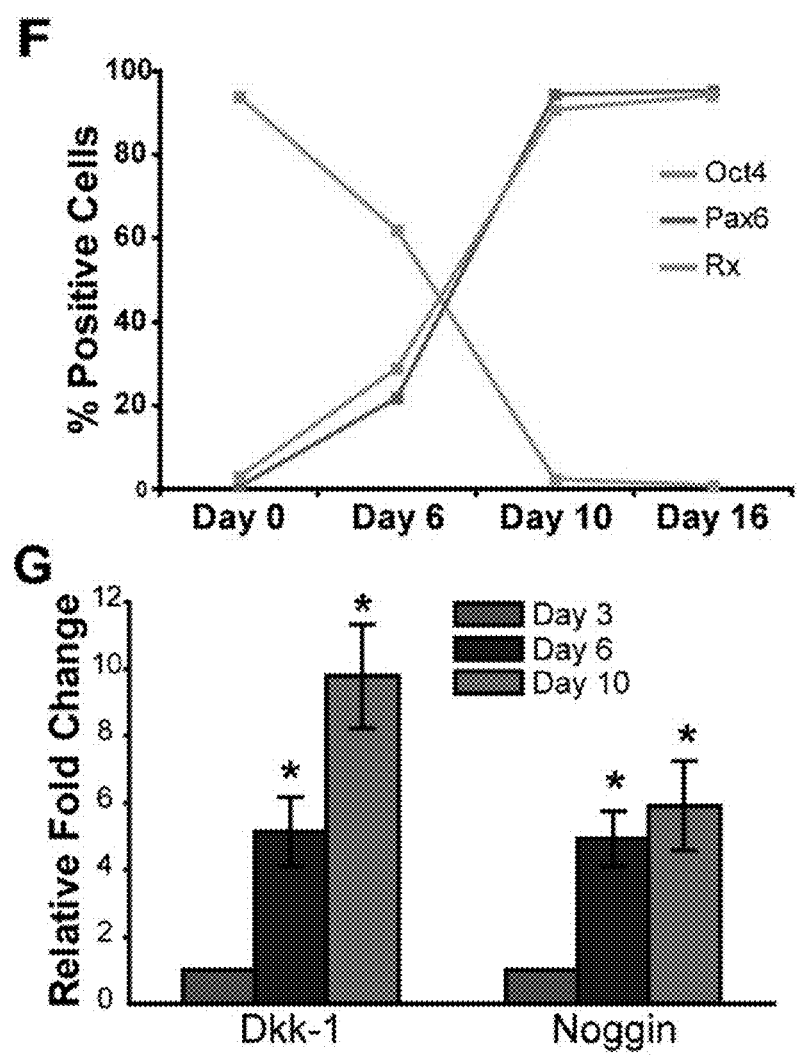
FIGS. 2A-2I, continued

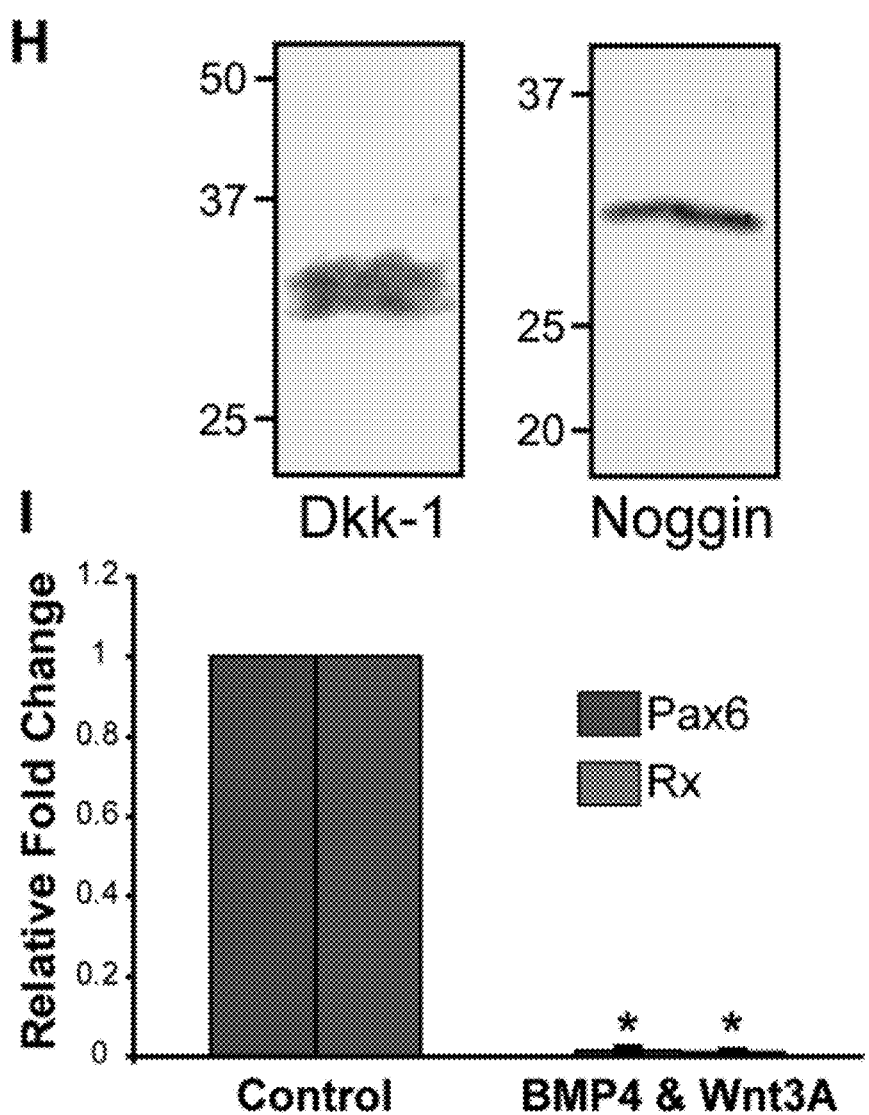
FIGS. 2A-2I, continued

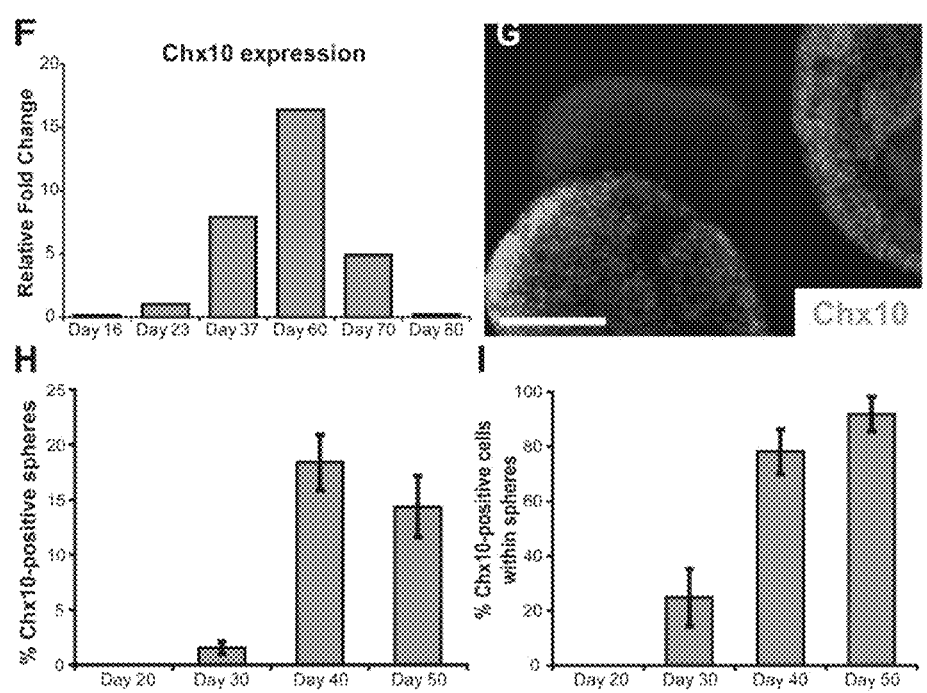
FIGS. 5A-5N, continued

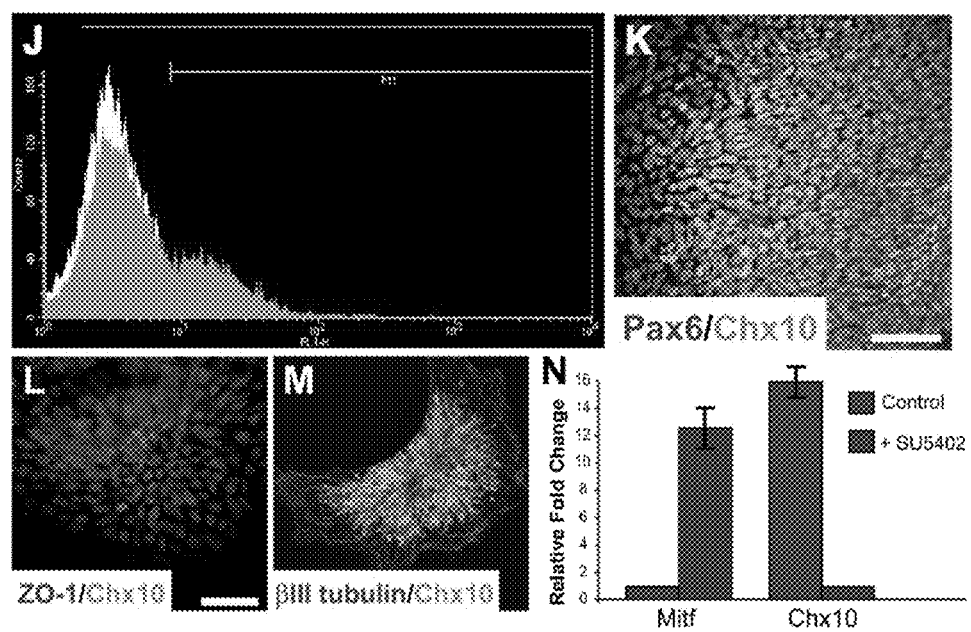
FIGS. 5A-5N, continued

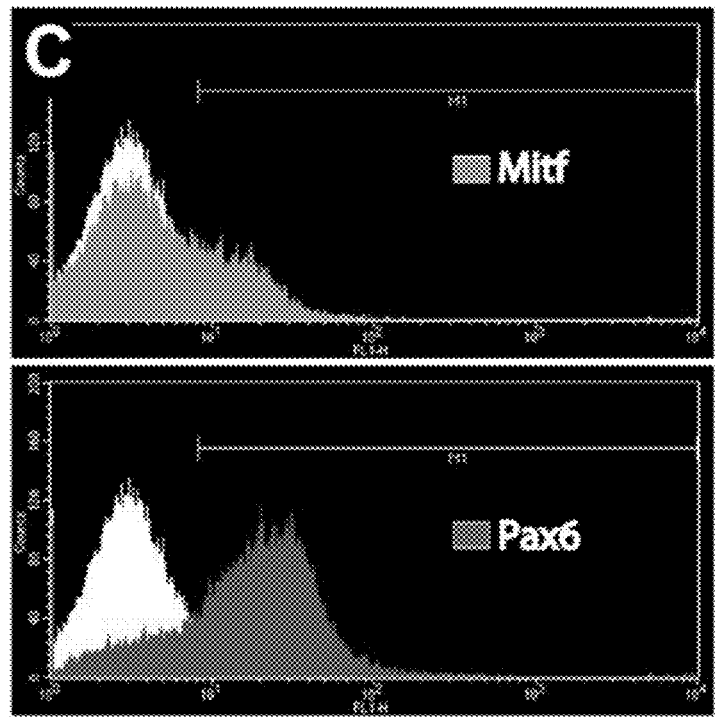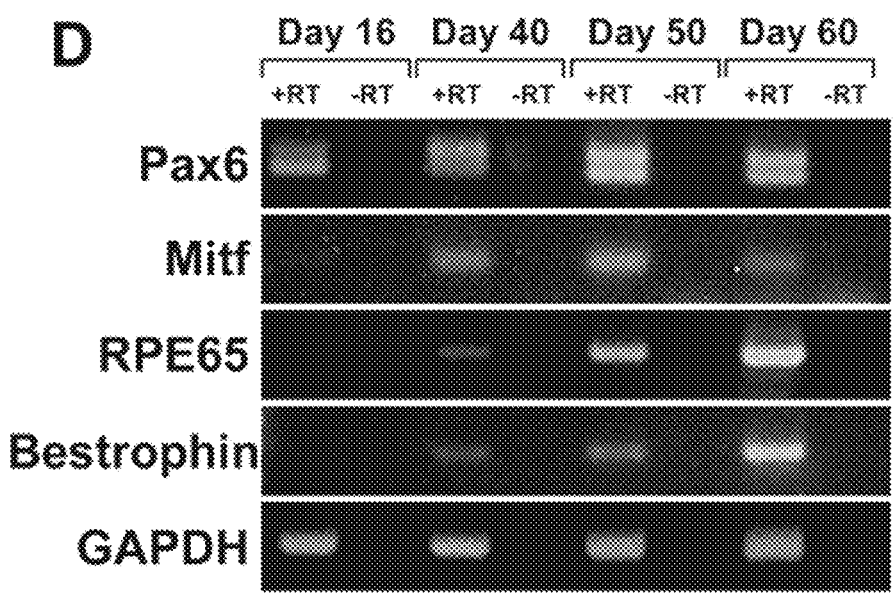
FIGS. 6A-6D, continued

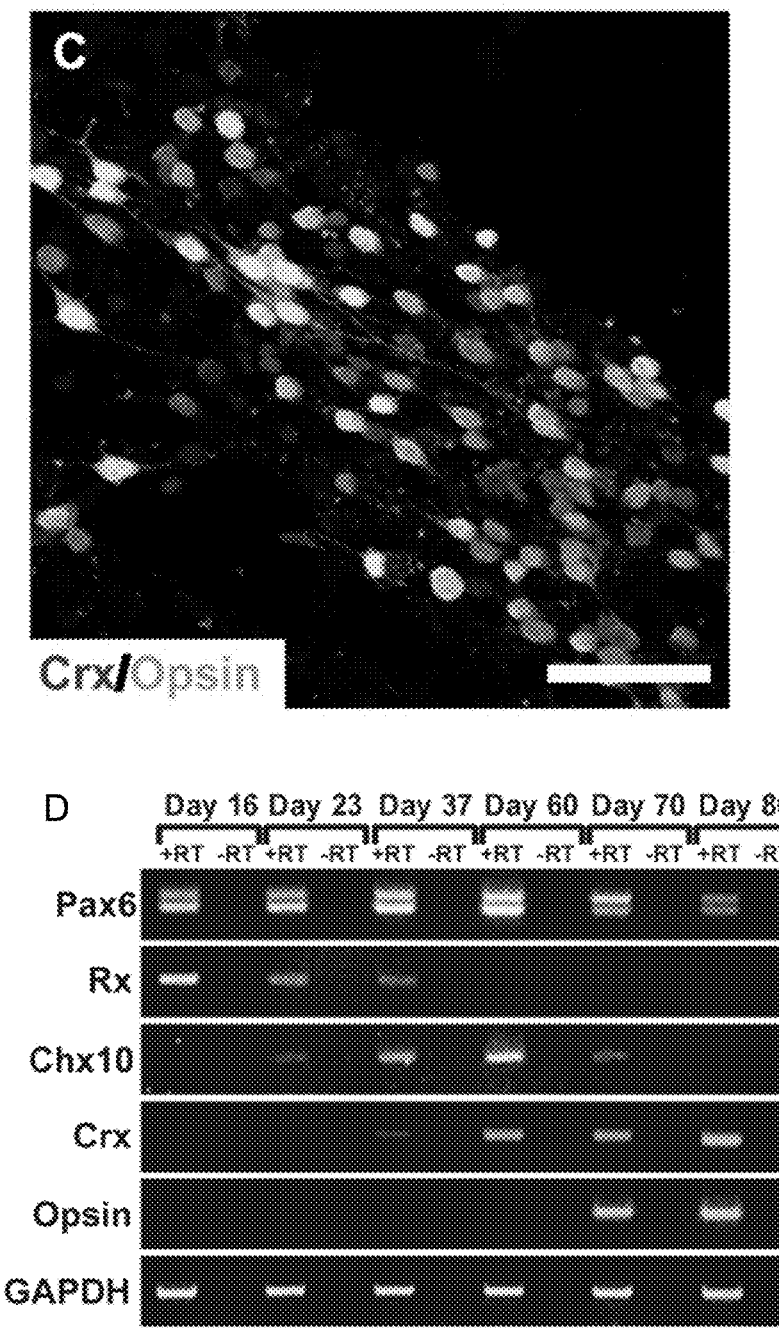
FIGS. 7A-7E, continued

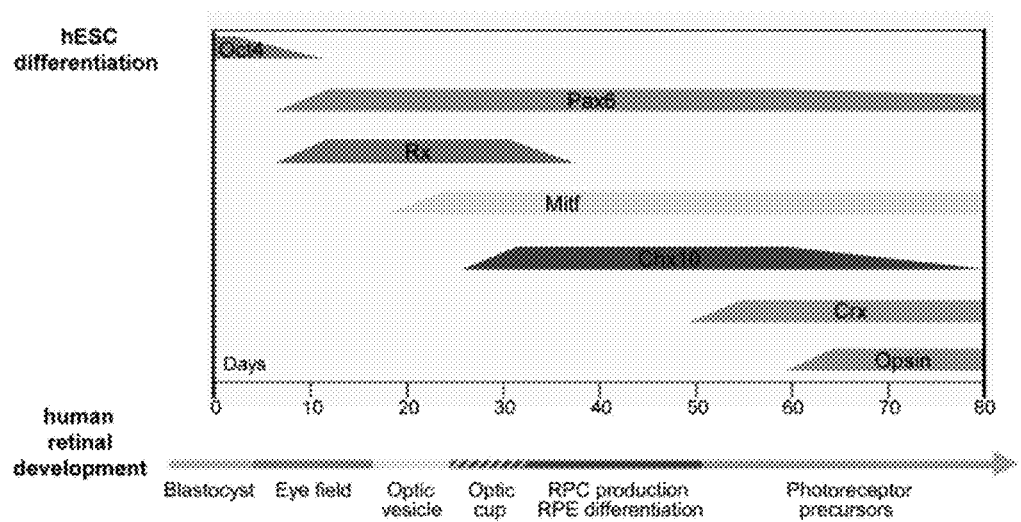
FIGS. 7A-7E, continued

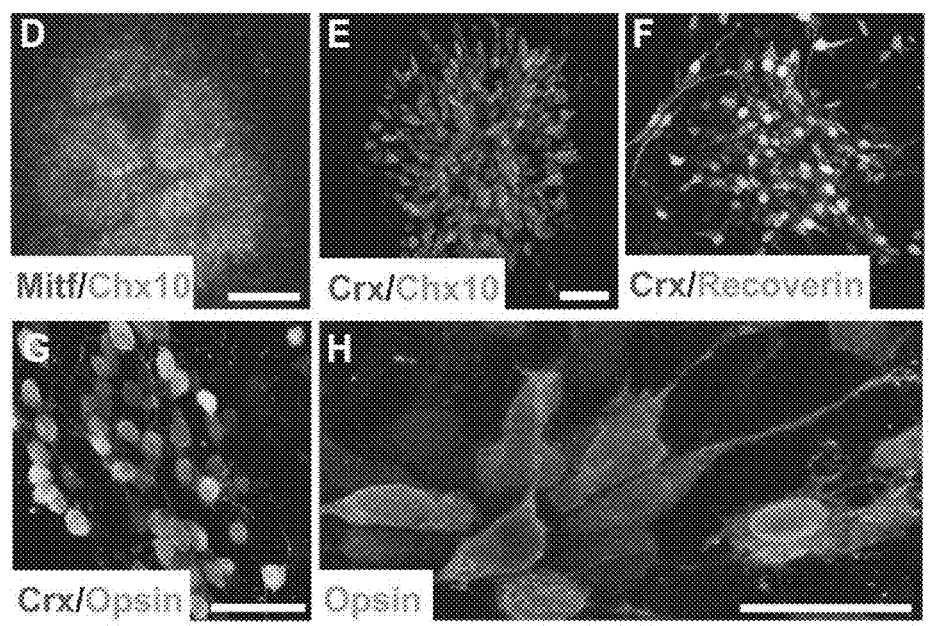
FIGS. 10A-10K, continued

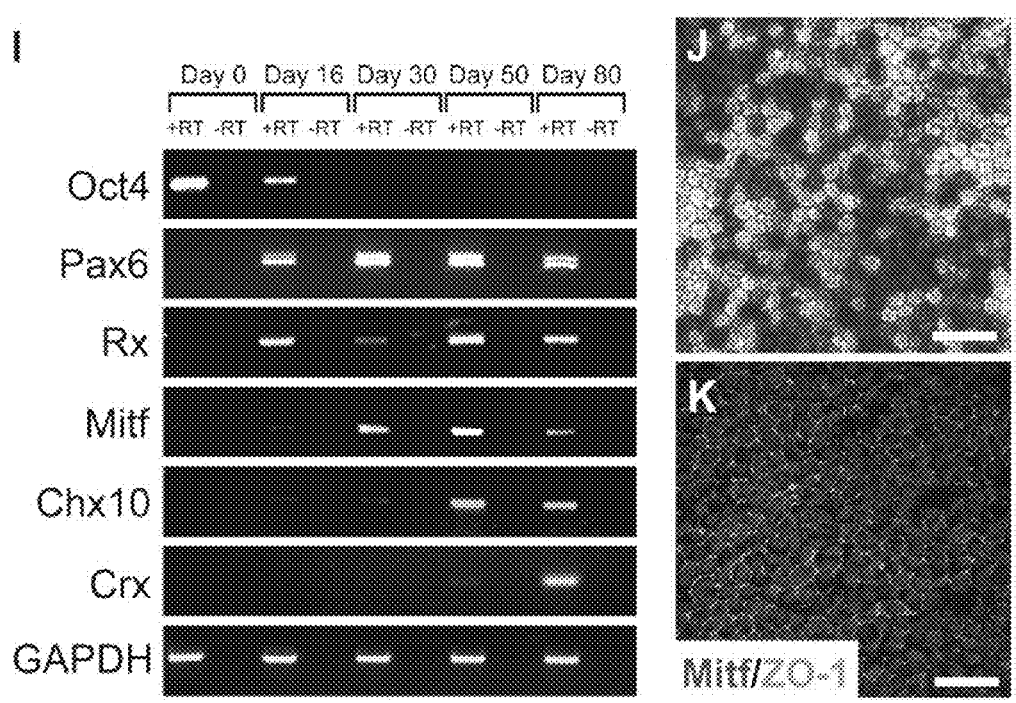
FIGS. 10A-10K, continued

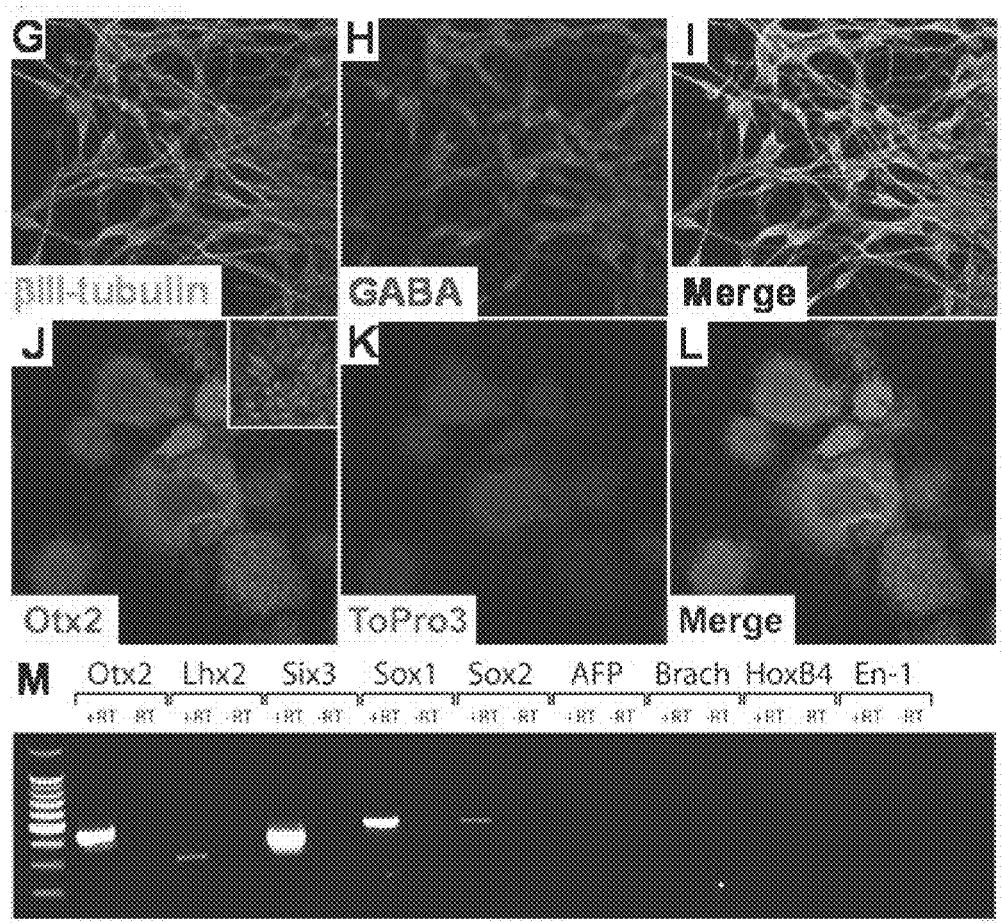
FIGS. 12A-12M, continued

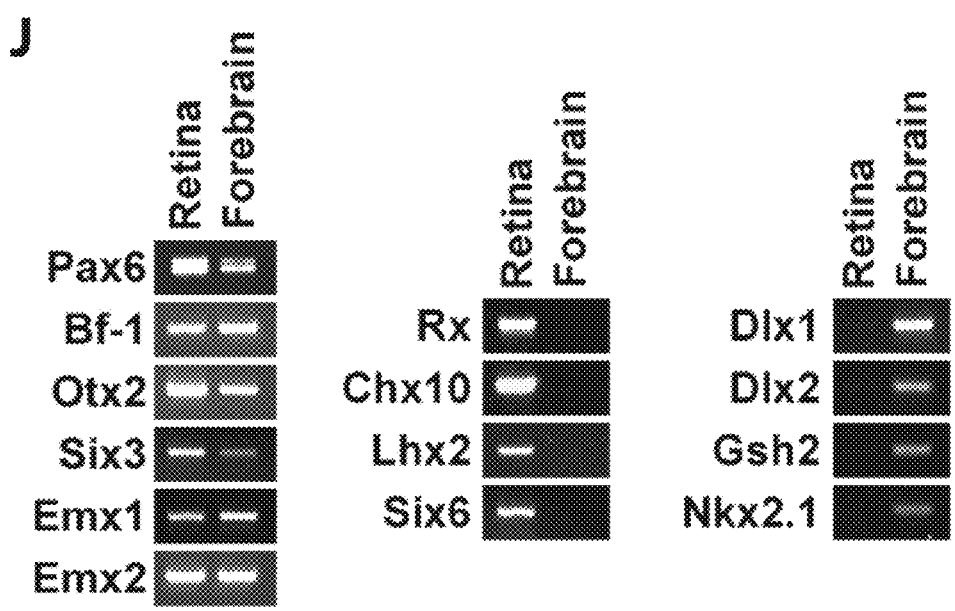
FIGS. 13A-13J, continued

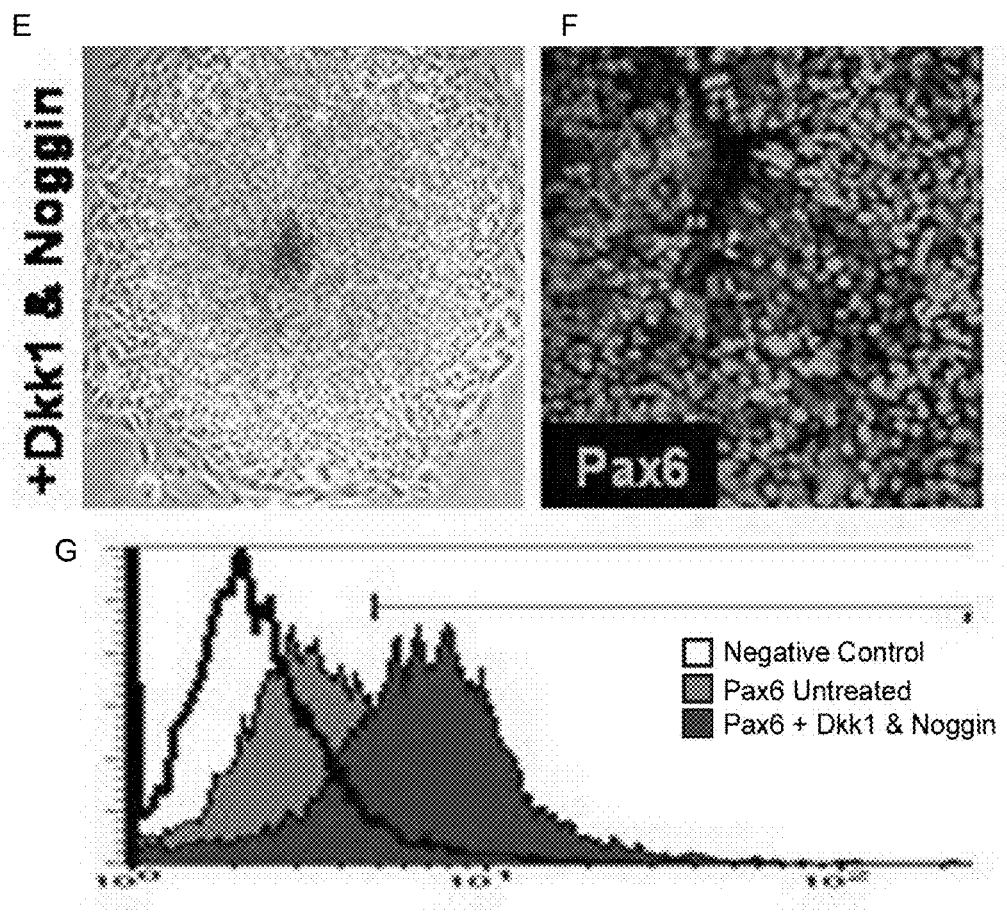
FIGS. 15A-15G, continued

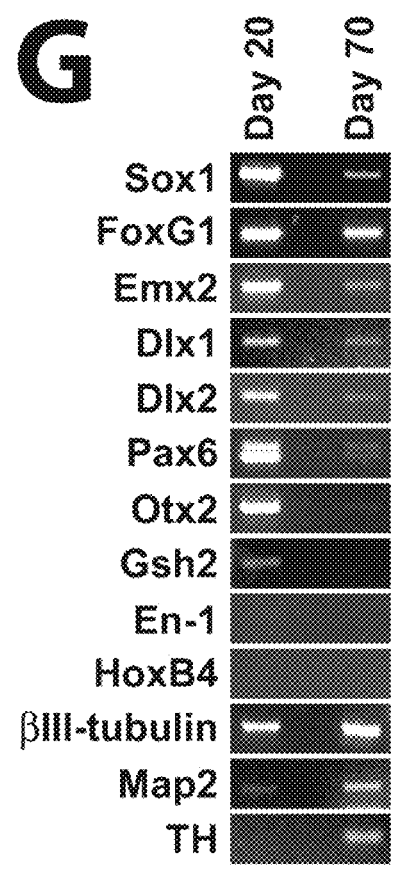
FIGS. 16A-16G, continued

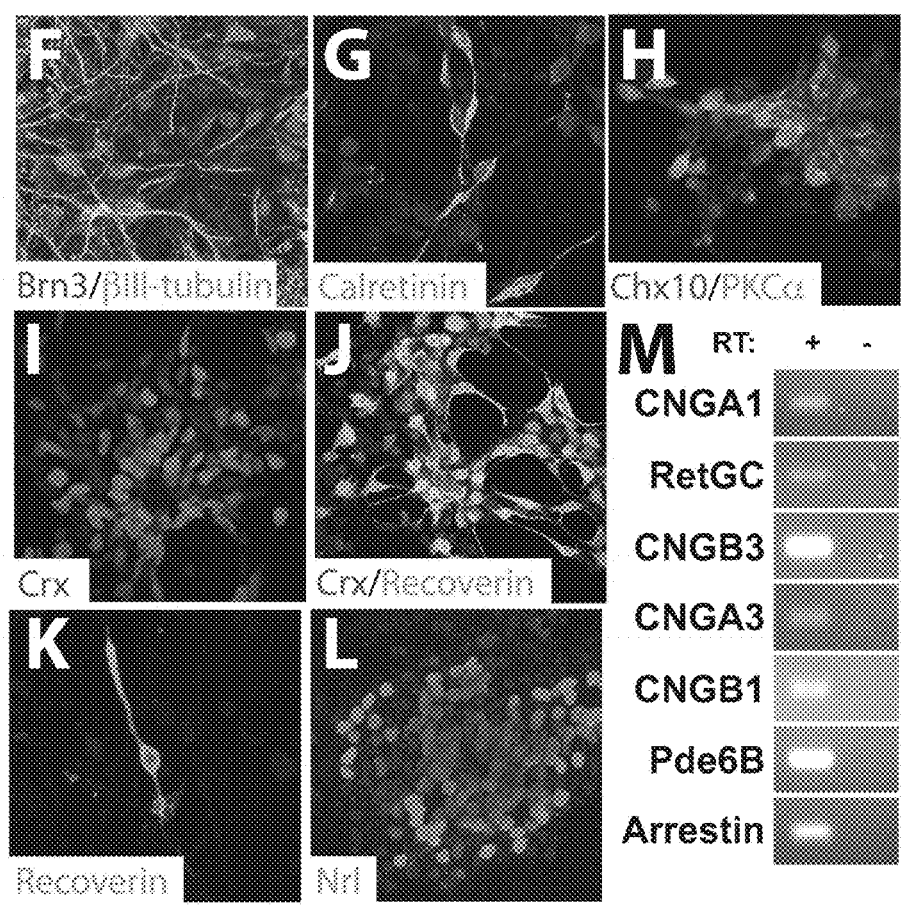
FIGS. 17A-17M, continued

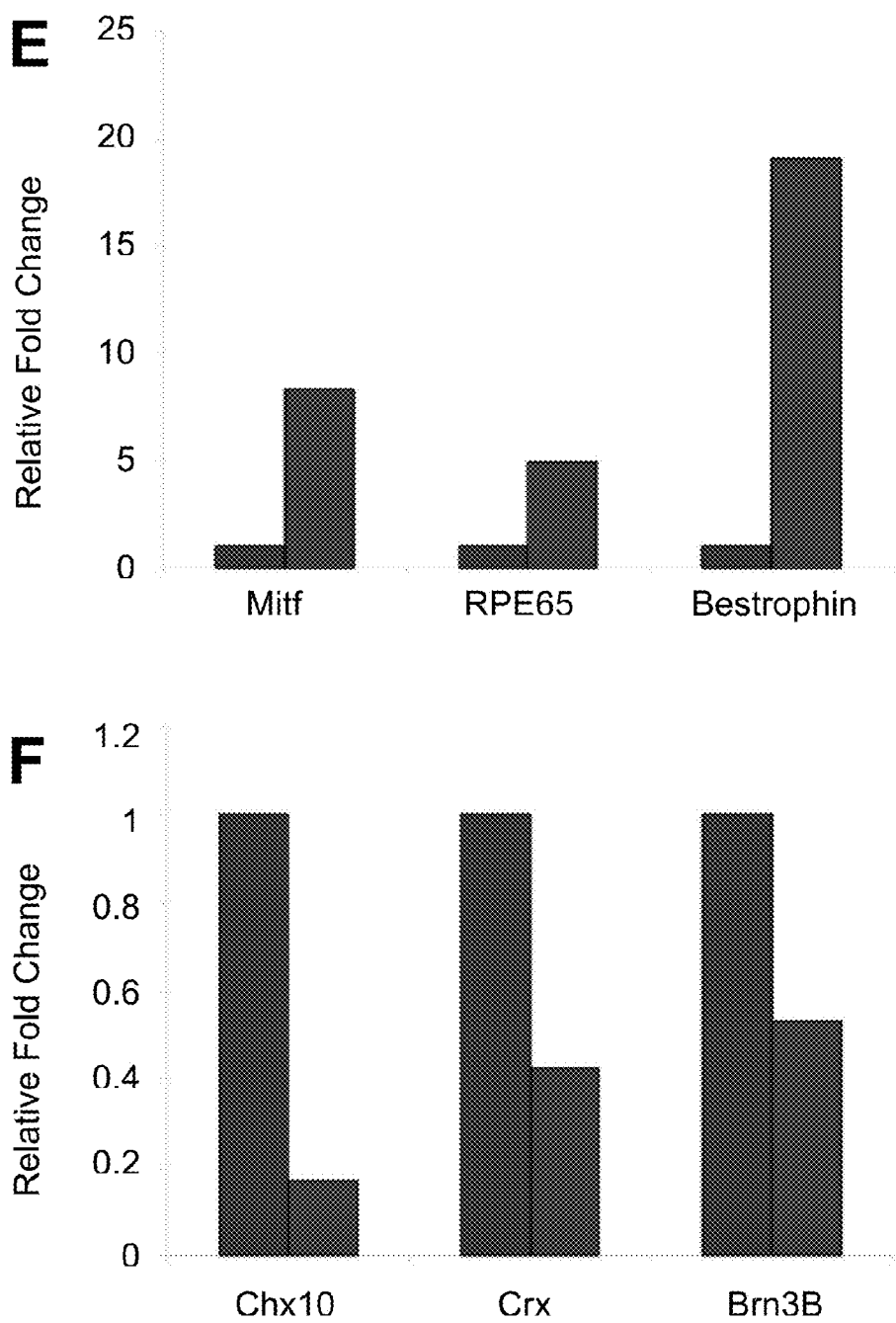
FIGS. 18A-18F, continued

SEQUENCE LISTING

<160> NUMBER OF SEQ ID NOS: 60

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
agaacctgtc acaagctgtg                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gacagcaagc tgaggatgtc                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gcgagaagat gacccagatc                                                    20

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 4
ccagtggtac ggccagagg                                                     19

<210> SEQ ID NO 5
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
atttataggc tggccctcac ggaa                                               24

<210> SEQ ID NO 6
<211> LENGTH: 24
<212> TYPE: DNA
<213> ORGANISM: Artificial Sequence
<220> FEATURE:
<223> OTHER INFORMATION: Synthetic olionucleotide

<400> SEQUENCE: 6
tgttctgccg gagtcataaa gcct                                               24

<210> SEQ ID NO 7
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 7
acccagttca tagcggtgac                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
caattgtcat gggattgcag                                              20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonuleotide

<400> SEQUENCE: 9
attcaacgaa gcccactacc caga                                         24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
atccttggct gacttgagga tgga                                         24

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
ggcgacacag gacaatcttt a                                            21

<210> SEQ ID NO 12
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 12
ttccggcagc tccgttttc                                               19

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 13
tattctgtca acgccttggc ccta                                         24
```

<210> SEQ ID NO 14
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 14
tgcatttagc cctccggttc ttga                                          24

<210> SEQ ID NO 15
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 15
agcaccttgg atgggtattc caga                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 16
acacaatcct gaggcacagt ctga                                          24

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
ccctggtttc tctgggactt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gcagtctgtg gggtcgtatt                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
accacagtcc atgccatcac                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
tccaccaccc tgttgctgta                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gcaaagagcc cgtcgtctac                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
cgtgtcaggt agcggttgta                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
caagatctcg gaccgctact                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ccgtggtcag catcttgtta                                              20

<210> SEQ ID NO 25
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 25
ttcacgagcg tcctgtatgc agat                                         24

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
ttgcaaagca ggatccatca agcc                                         24

<210> SEQ ID NO 27

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
caaaggcaaa caacccactt                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28
tctgctggag gctgaggtat                                              20

<210> SEQ ID NO 29
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 29
ccatcatttc cgagtgcaag tgct                                         24

<210> SEQ ID NO 30
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 30
aagctaggtc tctgtagccc agaa                                         24

<210> SEQ ID NO 31
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 31
cgagcaattt gccaagctcc tgaa                                         24

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
ttcgggcact gcaggaacaa attc                                         24

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
```

```
gtggaggaag ctgacaacaa                                                  20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
attctccagg ttgcctctca                                                  20

<210> SEQ ID NO 35
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 35
tacctggacc attggtattg gcgt                                             24

<210> SEQ ID NO 36
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 36
taagtccagc ccatggttac ggtt                                             24

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
caacagcaga atggaggtca                                                  20

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
ctgggtggaa agagagaagc tg                                               22

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
cggagtgaat cagctcggtg                                                  20

<210> SEQ ID NO 40
<211> LENGTH: 23
<212> TYPE: DNA
```

<213> ORGANISM: Artificial Sequence
<220> FEATURE:
<223> OTHER INFORMATION: Synthetic oligonucleotide

<400> SEQUENCE: 40
ccgcttatac tgggctatttt tgc                                    23

<210> SEQ ID NO 41
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 41
agtgaatcag ctcggtggtg tctt                                    24

<210> SEQ ID NO 42
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 42
tgcagaattc gggaaatgtc gcac                                    24

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
ctcggtggtg tctttgtcaa c                                       21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
acttttgcat ctgcatgggt c                                       21

<210> SEQ ID NO 45
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 45
gccctcctgc acaagtttga cttt                                    24

<210> SEQ ID NO 46
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 46
agttggtctc tgtgcaagcg tagt                                    24

<210> SEQ ID NO 47
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 47
gaatctcgaa atctcagccc                                                    20

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48
cttcactaat ttgctcagga c                                                  21

<210> SEQ ID NO 49
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 49
agcgaaactg tcagaggagg aaca                                               24

<210> SEQ ID NO 50
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 50
tcatgcagct ggtacgtggt gaaa                                               24

<210> SEQ ID NO 51
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 51
cgagcagaag acgcattgct tcaa                                               24

<210> SEQ ID NO 52
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 52
cggccttggc tatcatacat caca                                               24

<210> SEQ ID NO 53
<211> LENGTH: 24
<212> TYPE: DNA
<213> ORGANISM: Artificial Sequence
<220> FEATURE:

<223> OTHER INFORMATION: Synthetic oligonucleotide

<400> SEQUENCE: 53
atttgggacg gcgaacagaa gaca                                    24

<210> SEQ ID NO 54
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 54
atcctggatg ggcaactcag atgt                                    24

<210> SEQ ID NO 55
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 55
caatgcgggg aggagaagtc                                         20

<210> SEQ ID NO 56
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 56
ctctggacca aactgtggcg                                         20

<210> SEQ ID NO 57
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 57
cccccggcgg caatagca                                           18

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tcggcgccgg ggagatacat                                         20

<210> SEQ ID NO 59
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 59
atggcaaatt ctgtggcgct gaag                                    24

-continued

```
<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 60
gcgctgattt cccaagtgca ttct                                              24
```

SUBSTANTIALLY PURE HUMAN RETINAL PROGENITOR, FOREBRAIN PROGENITOR, AND RETINAL PIGMENT EPITHELIUM CELL CULTURES AND METHODS OF MAKING THE SAME

CROSS-REFERENCE TO RELATED APPLICATIONS

This application is a divisional of U.S. application Ser. No. 12/806,907, filed Aug. 24, 2010, that will grant as U.S. Pat. No. 9,328,328 on May 3, 2016, which claims the benefit of U.S. Provisional Application No. 61/274,962, filed on Aug. 24, 2009, each of which is incorporated by reference herein in its entirety.

STATEMENT REGARDING FEDERALLY SPONSORED RESEARCH OR DEVELOPMENT

This invention was made with government support under MSN116835 awarded by the National Eye Institute. The government has certain rights in the invention.

BACKGROUND

In human development, the genesis and further differentiation of retinal tissue follows a well-defined and conserved developmental program, with numerous markers available to distinguish the major stages of retinogenesis. Retinogenesis begins within the first few weeks of human development, when a portion of the primitive anterior neuroepithelium gives rise to the paired eye fields (Li, H., et al., 1997; Mathers, P. H., et al., 2000; Bailey, T. J., et al., 2004; Zuber, M. E., et al., 2003). The eye fields are made up of a cell population characterized by the expression of numerous transcription factors, including Pax6, Rx, Otx2, Six3, Six6, Tll and Lhx2. Although Pax6 and Rx have been used to identify retinal progenitor cells (RPC) in differentiating embryonic stem cell (ESC) cultures (Osakada, F., et al., 2008; Mathers, P. H., et al., 2000), during development Pax6 and Rx are initially co-expressed in a broad region of the anterior neural plate that includes the eye field and future forebrain (Mathers, P. H., et al., 2000). Thereafter, Pax6+/Rx+ cells become restricted to more specific areas of the developing CNS (Mathers, P. H., et al., 2000), predominantly the retina (Bailey, T. J., et al., 2004; Furukawa, T., et al., 1997b). The remaining cells predominantly develop into forebrain structures.

The next in vivo retinal specification phase involves formation of optic vesicles from the paired eye fields. After the optic vesicles evaginate from the paired eye fields, all cells that will give rise to either the neural retina or the retinal pigment epithelium (RPE) express the transcription factor Mitf (Chow, R. L., et al., 2001; Bharti, K., et al., 2008).

The subset of Mitf+ cells destined to become neural retina or retinal pigment epithelium subsequently downregulate Mitf in response to the onset of expression of Chx10, also called Vsx2 (Horsford, D. J., et al., 2005; Rowan, S., et al., 2004). Neural retinal progenitors destined for the inner layer of the optic cup express Chx10 and downregulate Mitf in response to fibroblast growth factors (FGFs) secreted by the overlying surface ectoderm. Thus, Chx10 is the earliest specific marker of neural RPC within the optic vesicle and cup (Rowan, S., et al., 2004). Chx10+ retinal progenitors give rise to all cell types of the neural retina: cones, rods, ganglion cells, amacrine cells, bipolar cells, horizontal cells and Muller glia. Conversely, cells destined for the outer layer of the optic cup remain Mitf+ and Chx10-negative and subsequently differentiate into RPE.

Among the first differentiated neural retinal phenotypes observed during development are cone photoreceptors (Barishak, Y., 2001; Finlay, B. L., 2008), whose precursors express the primitive cone and rod photoreceptor-specific transcription factor Crx (Chen, S., et al., 1997; Furukawa, T., et al., 1997). Later, cones express recoverin and ultimately opsin. Rod photoreceptors express the transcription factor Nrl followed by the phototransduction molecules recoverin and rhodopsin. Retinal ganglion cells are also produced early on, and can be distinguished among developing retinal cells by their expression of βIII tubulin and HuC/D and by their long processes. Other retinal neurons such as bipolar cells, horizontal cells and amacrine cells have markers as well (PKCα, calbindin and calretinin, respectively). Again, however, these markers are found elsewhere in the central nervous system, so it is imperative that the population from which they arise be established as neural retinal progenitors (Chx10+/Pax6+), which themselves come from optic vesicle and eye field cells.

Retinal development is of particular interest to clinicians and researchers, because millions of individuals in North America suffer varying degrees of irreversible vision loss as a result of retinal degenerative disease (RDD). Inherited and acquired outer RDDs, such as retinitis pigmentosa (RP) and age-related macular degeneration (AMD), are major causes of progressive vision loss for which there are no cures and few therapeutic options. In such disorders, rod and cone photoreceptor cells and adjacent retinal pigment epithelium (RPE) cells in the outer retina are most affected. Inner RDDs predominantly affect retinal ganglion cells, causing glaucoma and other diseases that result in permanent vision loss. During the early and middle stages of RDD, treatment focuses on rescuing at-risk cells and preserving visual function. After an RDD results in a critical level of cell death, suitable treatment approaches are limited to bypassing or replacing lost cells while mitigating the underlying disease process.

Because neural tissue is generally not self-regenerating, successfully treating any neurodegenerative disease is difficult. However, because the outer retina is easily accessible and contains a comparatively simple network of short-range intercellular connections, the outer retina is a more favorable treatment target than most other central nervous system tissue.

MacLaren et al. (Nature, 2006, 444:203-207) demonstrated therapeutic replacement of outer retinal cells in a mouse RP model by showing that rod precursor allografts could integrate and restore partial retinal function. McLaren's proof of concept spurred efforts to find comparably capable sources of human cells having the potential to expand in culture and differentiate into multiple retinal cell types. However, cells from proposed sources often have characteristics that significantly limit potential clinical use. For example, human fetal retinal progenitor cells (RPC) have been propagated in culture, but over time, the cells became progressively restricted to a glial fate, necessitating gene misexpression to generate neuronal cell types (Gamm et al, Stem Cells 2008). Similarly, RPE, iris pigment epithelium and non-ocular stem and progenitor cells often lack a definitive capacity to produce retinal cells, and the existence of a multipotent retinal stem cell population in adult human pigmented ciliary epithelium was recently called into question (Cicero et al., 2009; Gualdoni et al, 2010).

Although human fetal forebrain progenitors have proven to be effective for reducing anatomical and functional photoreceptor loss and visual decline after subretinal transplantation in rodent models of RDD (likely due to their ability to secrete natural neuroprotective factors), finding human sources that work for retinal cell replacement has been problematic.

The successful culturing of human pluripotent stem cells, including both embryonic stem cells (ESC) and induced pluripotent stem cells (iPSC), has provided an intriguing and potentially inexhaustible supply of cells with regenerative potential. Additionally, human ESC and iPSC have potential as research tools for studying the developmental steps leading to the production of retinal cell types, the most important being photoreceptors (cones and rods), ganglion cells and RPE. More detailed knowledge of the steps involved in the differentiation of these and other retinal cell types would be useful for both basic science and clinical studies, as it would improve cell production efficiency, reproducibility, and perhaps also cell function.

Furthermore, if they can be used to provide model systems that successfully replicate human retinogenesis in vivo, human ESC and iPSC cells could potentially provide a powerful tool for examining early human retinal and neural cell development at stages that were previously inaccessible. One criterion for assessing pluripotent stem cell-based developmental model systems is the capacity to recapitulate the normal embryonic maturation sequence in a controlled, stepwise fashion (Keller, G., 2005; Pera, M. F., et al., 2004). Such systems should also provide the opportunity to test the effects of developmental stimuli and enrich for early cell populations to reduce contamination from undesired and/or unidentified cell lineages. It would also be advantageous to monitor cellular maturation by marker expression to ascertain whether developmental checkpoints are met in order and according to a predictable timeline.

Human iPSC are a subclass of human pluripotent cells created by reprogramming somatic cells such as skin fibroblasts or other mature cell types to a pluripotent state by transiently misexpressing a few select genes (Takahashi, K., et al., 2007; Yu, J., et al., 2007). Early studies indicate that human iPSC can have widely varying innate potential to produce neuroepithelial cells, the predecessors of all retinal cell types (Hu et al., 2010, Yu et al., 2007; Hirami et al., 2009). Because the differentiated cells derived from iPSC are genetically identical to the adult cells from which the iPSC are derived, iPSC have a potential advantage over ESC in certain therapeutic or research applications. For example, IPSC technology offers an alternative to human ESC differentiation wherein it is envisioned that one can produce iPSC from somatic cells of an individual and then treat the same individual with cells (e.g., retinal lineage cells) obtained by differentiating the iPSC. In addition, individual-specific pluripotent iPSC lines can be used to develop in vitro models of human diseases. (Ebert, A. D., et al, 2009; Park, I. H., et al, 2008).

The therapeutic and research potential of human ESC and human iPSC would be enhanced if the earliest committed cells in the retinal lineage could be isolated from unwanted or contaminating cell types into a substantially pure cell culture. This is particularly the case for retinal neurons, which, with the exception of photoreceptors, cannot be unequivocally identified unless one is sure that they were derived from retinal progenitor cells. Similarly, the study and use of human ESC- and iPSC-derived forebrain cells would be aided by a method that produces enriched populations of these cells at a very early stage of differentiation.

Current methods for differentiating pluripotent cells into cell types of interest have limited clinical and scientific appeal due to contamination from early, unwanted cell types and a lack of information regarding the key steps involved in genesis of the differentiated cells. Existing methods have focused on deriving mixed retinal cell populations or more mature cells such as RPE (U.S. Pat. Nos. 7,541,186 and 7,736,896; Klimanskaya, I., et al., 2004; Vugler, A, et al., 2008; Clegg et al., 2009) or photoreceptors (Osakada, F., et al., 2008) using various exogenous factors to increase the percentage of early retinal cell types in the heterogeneous population of differentiating human ESC. For example, retinoic acid and taurine can induce human ESC to differentiate to photoreceptor-like cells (Osakada, F., et al., 2008). However, no one has described a method for differentiating human pluripotent cells into a highly enriched, isolated population of early retinal progenitor cells (RPC) that can progress through the major retinal developmental stages leading to production of mature cell types. Furthermore, retinal cell types produced thus far have not exhibited a differentiation time course comparable to that observed in normal human retinogenesis. Indeed, the timing of appearance in culture of selected retinal development stages has varied widely among published protocols (Banin, E., et al., 2006; Lamba, D A., et al., 2006; Osakada, F., et al., 2008; Klassen, H., et al., 2008). For example, the reported onset of expression of the Crx marker has ranged from one to thirteen weeks, depending on the protocol used (Lamba, D A., et al., 2006; Osakada, F., et al., 2008).

Thus, there is a need in the art for substantially pure cultures of certain human neuroepithelial lineage cells, including retinal progenitor cells, forebrain progenitor cells, and retinal pigment epithelium cells, that accurately model in vitro differentiation and development, and for simplified methods of producing such cultures.

BRIEF SUMMARY OF THE INVENTION

The present invention relates generally to methods for producing populations of neural RPC, RPE and forebrain progenitors (all derivatives of anterior neurepithelium) from human pluripotent cells, and for the substantially purified cell populations that can be produced using the methods. Advantageously, the disclosed methods for making the populations do not rely upon genetic manipulation of the differentiating cells, nor the use of reporter gene constructs or other molecular tools to isolate the desired cells.

In a first aspect, the invention encompasses a substantially pure cell culture of human neuroepithelial lineage cells. The culture contains one or more human neuroepithelial lineage cells. The neuroepithelial lineage cells are human retinal progenitor cells, human forebrain progenitor cells, or human retinal pigmented epithelium cells. The selected neuroepithelial lineage cell type comprises at least 90% of the cells present in the culture. The cell culture additionally contains a suitable medium for maintaining the viability of the human neuroepithelial lineage cells.

In some embodiments, the selected neuroepithelial lineage cell type comprises at least 95% of the cells present in the culture. In such embodiments, the human neuroepithelial lineage cells are preferably derived from embryonic stem cells.

In some preferred embodiments, the human retinal lineage cells are in the form of neurospheres. The neurospheres may be maintained suspended within the culture and not attached to a surface, or they may be maintained plated onto a surface.

In certain embodiments, the human retinal lineage cells that are contained in the culture are human retinal progenitor cells that are Chx 10-positive. In other embodiments, the human retinal lineage cells are human forebrain progenitor cells that are Otx 2-positive.

Optionally, the culture is serum free. Preferably, the human neuroepithelial lineage cells contained in the culture are derived from non-fetal cells. More preferably, the human neuroepithelial lineage cells are derived from embryonic stem cells or induced pluripotent stem cells.

In certain embodiments, the human neuroepithelial lineage cells are human retinal pigmented epithelium cells derived from human induced pluripotent stem cells.

In a second aspect, the invention encompasses a method of separating neuroepithelial lineage cells by progenitor cell type. The method includes the steps of (a) culturing two or more detached human neuroepithelial rosettes derived from non-fetal cells in suspension until neurospheres of at least two different progenitor cell types form, (b) observing one or more morphological characteristic of the neurospheres to identify the progenitor cell types of the neurospheres, and (c) mechanically separating the neurospheres by progenitor cell type.

Preferably, the detached human neuroepithelial rosettes are derived from human pluripotent cells. More preferably, the human pluripotent cells from which the detached human neuroepithelial rosettes are derived are embryonic stem cells or induced pluripotent stem cells. In some embodiments where the detached human neuroepithelial rosettes are derived from induced pluripotent stem cells, the induced pluripotent stem cells are obtained by reprogramming somatic cells from an individual to pluripotency. In certain embodiments, the detached human neuroepithelial rosettes are obtained by reprogramming IMR90 cells to pluripotency. In some embodiments where the detached human neuroepithelial rosettes are derived from embryonic stem cells, the embryonic stem cells from which the detached human neuroepithelial rosettes are derived are H1 line cells or H9 line cells.

Preferably, the step of mechanically separating the neurospheres by progenitor cell type is performed before the neurospheres of at least two different progenitor cell types begin to aggregate together.

In some embodiments, the step of culturing the two or more detached human neuroepithelial rosettes occurs in a retinal differentiation medium.

In certain embodiments, the different progenitor cell types that are mechanically separated are retinal progenitor cells and forebrain progenitor cells. In some such embodiments, the neurospheres observed to have a vesicular laminar morphology are identified as retinal progenitor cells and the neurospheres observed to have a uniform morphology are identified as forebrain progenitor cells. Preferably, the morphological characteristics of the neurospheres are observed using bright field microscopy. Optionally, the retinal progenitor cell neurospheres are mechanically separated from the forebrain progenitor cell neurospheres to form a substantially pure culture of retinal progenitor cell neurospheres, or the forebrain progenitor cell neurospheres are separated from the retinal progenitor cell neurospheres to form a substantially pure culture of forebrain progenitor cell neurospheres.

In certain embodiments, the retinal progenitor cell neurospheres in the substantially pure culture produced by the method may be further cultured until they differentiate to photoreceptors, ganglion cells, and other neural retinal cell types. Preferably, the retinal progenitor cell neurospheres are cultured in the substantially pure culture with retinal differentiation medium until retinal pigment epithelium cell neurospheres form. In some such embodiments, the detached human neuroepithelial rosettes used are derived from induced pluripotent stem cells, preferably obtained by reprogramming somatic cells from an individual to pluripotency, and the step of culturing the retinal progenitor cell neurospheres takes place in the presence of Activin. Optionally, such embodiments further includes the step of mechanically separating the retinal pigment epithelium cell neurospheres from the rest of the culture to form a substantially pure culture of retinal pigment epithelium cells. The retinal pigment epithelium cell neurospheres may optionally be cultured onto laminin-coated culture dishes.

The invention further encompasses a substantially pure culture of retinal progenitor cell neurospheres, forebrain progenitor cell neurospheres or retinal pigment epithelium cells, as produced by the various embodiments of the method that are described above.

The methods and cell cultures of the invention are further detailed below.

BRIEF DESCRIPTION OF DRAWINGS

This patent application file contains at least one drawing executed in color. Copies of this patent or patent application publication with color drawings will be provided by the Office upon request and payment of the necessary fee.

The invention will be better understood and features, aspects and advantages other than those set forth above will become apparent when consideration is given to the following detailed description thereof. Such detailed description makes reference to the following drawings.

FIGS. 2A-2I show highly efficient derivation of eye field phenotypes from human ESC. (A) RT-PCR analysis showing the onset of Pax6 and Rx gene expression and concomitant loss of Oct4. (B-C) qPCR analysis of Oct4 gene expression (B) and Pax6 and Rx gene expression (C). Values were expressed as fold change relative to undifferentiated human ESC. (D) Immunocytochemical analysis of cells at day 10 showing uniform coexpression of Pax6 and Rx. (E) FACS analysis confirming the rapid loss of Oct4 expression and the onset of both Pax6 and Rx protein expression. Negative controls for FACS analyses are indicated by the white histograms. (F) Quantification of the FACS analysis. (G-H) qPCR (G) and Western analysis (H) demonstrating the endogenous expression of the BMP and Wnt antagonists Noggin and Dkk-1. (I) qPCR showing the near complete loss of Pax6 and Rx gene expression in cells treated with BMP4 and Wnt3A. Scale bar equals 40 μm.

FIG. 13J results for isolated cultures of vesicular neurospheres are labeled "Retina," and results for isolated cultures of non-vesicular neurospheres are labeled "Forebrain."

Figures 1A, 1B, 1C, 1D, 1E, 1F:
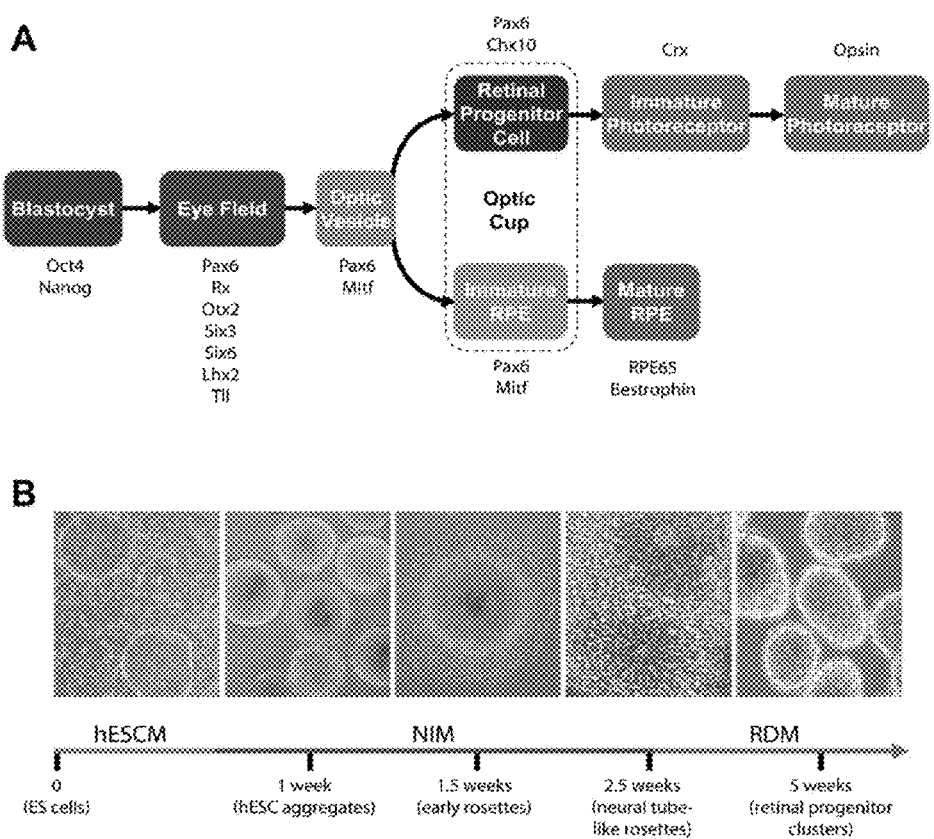
FIGS. 1A-1F show the stepwise development towards a retinal lineage, beginning with the establishment of the eye field within the anterior neuroepithelium. (A) Each major stage in retinogenesis can be distinguished in part based upon the expression of various transcription factors. (B) Schematic of the differentiation protocol used to generate cells of a retinal lineage. (C) RT-PCR analysis of the changes in gene expression towards an eye field fate through the first 16 days of differentiation. (D-F) Immunocytochemistry of typical human ESC aggregates 10 days after differentiation, demonstrating the expression of the eye field transcription factors Otx2 (D) and Lhx2 (E) and the definitive neural transcription factor Sox1 (F). Scale bar equals 200 μm.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DESCRIPTION OF THE INVENTION

We have developed a novel and simplified protocol to both produce and isolate retinal progenitor cell (RPC) and forebrain progenitor cell (FPC) neurospheres from human pluripotent cells. Human ESC (e.g., lines H1 or H9) and iPSC (e.g., lines developed from an individual, or in this proof of concept, reprogrammed iPSC lines derived from somatic cell lines such as IMR90 fetal fibroblast cells, ATCC CCL-186) following this protocol undergo a targeted, stepwise differentiation process that follows a normal developmental timeline and initially yields highly enriched populations of eye field cells that eventually separate into discrete, morphologically distinct RPC and FPC cell populations that can be mechanically isolated from one another as highly enriched or substantially pure neurosphere cultures. Thereafter, the RPC neurospheres acquire features of advancing retinal differentiation, including production of RPE neurospheres, in a sequence and time course that mimic in vivo human retinal development. The resulting RPE neurospheres can also be mechanically separated to produce a culture of enriched or substantially pure RPE.

Accordingly, the invention encompasses both methods for separating neuroepithelial lineage cells by progenitor cell type and the substantially pure cultures of human neuroepithelial lineage cells that can be produced by such methods.

It is envisioned that the methods and substantially pure cell cultures of the present invention are useful in the following areas:

1. Transplantation. Non-limiting examples include the use of FPC in therapeutic cell rescue therapy, and the use of RPC, RPE, FPC or cells differentiated from any of the foregoing in lost cells replacement therapy to help restore previously lost vision. The methods and cultures could also be used for developing tissues for use in whole tissue replacement therapy.

2. Drug screening for agents to protect or enhance the function of all cells, including ganglion cells, rods, cones, RPE, forebrain cells, and midbrain cells.

3. Producing retinal disease models from pluripotent cells, especially from iPSC, which can also be used to study pathophysiology and for drug screening or customized therapy using stem cells or derivatives thereof.

4. As a unique model of human neural development, which would be a useful resource to study a variety of processes, including without limitation retinal development, tissue formation, and synapse formation.

The protocol used for generating neuroepithelial rosettes from human ESC or iPSC is as follows. First, human ESC or iPSC lifted from an irradiated mouse embryonic fibroblast (MEF) cell layer are grown as aggregates in suspension in embryonic stem cell medium (ESCM) without fibroblast growth factor 2 (FGF2) for four days. In a non-limiting example, ESCM contains DMEM/F12 (1:1) (Gibco #11330-065), 20% knockout serum replacement (Gibco #10828-028), 0.1 mM 13 mercaptoethanol, 1 mM L-glutamine (Gibco #25030-081), 1% MEM nonessential amino acids (Gibco #11140-050), and 4 ng/mL FGF2 (Invitrogen #13256-029). The pluripotent cells can alternatively be cultured using a defined medium such as TESR medium using a matrix such as Matrigel, or under other conditions known to support culture of such cells. The aggregates are then cultured in a chemically defined neural induction medium (NIM) for two days. The aggregates are then allowed to attach to the surface of the culture dish, preferably with the addition of laminin. By about day 15, columnar cells will have developed which often form neuroepithelial structures.

The invention relates to various methods for producing and isolating other retinal lineage cells, including RPC, FPC and RPE, from the neuroepithelial rosettes. On about day 16 of differentiation, the neuroepithelial rosettes can be mechanically detached from adherent cultures with light trituration upon change of medium and placed into suspension culture in non-adherent culture dishes. Over the next 24-48 hours, sphere-like cell aggregates (neurospheres) highly enriched for RPC and FPC form. Within three to five days after detachment, using, e.g., a polished Pasteur pipette, one can mechanically separate and isolate the RPC neurospheres and FPC neurospheres, based on the observed morphological differences that appear between the two neurosphere types (See FIGS. 13 A-C).

Specifically, RPC neurospheres appear phase-bright and golden in color with a ring-like, outer pseudostratified, laminar structure (a "vesicular" or "laminar" morphology) under bright field microscopy (FIG. 13 B), and FPC neurospheres appear more uniform in color and density under bright-field microscopy (a "non-vesicular" or "non-laminar" morphology; FIG. 13 C). If the two neurosphere populations are not separated in this short culture window following the appearance of these morphological differences, they will attach to one another and become inseparable.

The RPC and FPC neurospheres are maintained separately in flasks containing a Retinal Differentiation Medium (RDM). In a non-limiting example, RDM includes DMEM/F12 (3:1) supplemented with 2% B27. By mechanically separating the neurospheres according to these morphological differences, one can obtain a multipotent RPC neurosphere culture having greater than 90% purity as assessed by immunocytochemical analysis (e.g., Chx10), meaning that greater than 90% of the cells in the neurosphere culture are RPCs. In this disclosure, the term "substantially pure" culture refers a culture wherein at least 90% of the cells are of a given cell type. Other cells remaining in the culture are more primitive optic vesicle cells (expressing Mitf) or eye field cells (expressing Pax6, Rx and Lhx2). The FPC neurospheres in the other flask express neural and forebrain markers such as Otx2, Pax6, Sox1 and Sox2.

The RPC neurospheres begin to lose their unique morphological structure after 1 week in RDM and produce non-pigmented, Chx10+/Pax6+/Mitf-neural retinal neurosphere populations. These neurospheres in turn yield Crx+/recoverin+/opsin+ and Nrl+ photoreceptors and βIII tubulin+/Brn3/HuC-D+ retinal ganglion cells in a sequence and time frame that mimics normal human retinogenesis.

In addition to the non-pigmented neurosphere populations, the RPC neurospheres produce pigmented, Mitf+/Chx10-RPE neurospheres, the latter of which are identifiable in culture by about day 30-50 of overall differentiation. As they are brown-black in color, they can then be mechanically removed from the remaining neural RPC neurospheres and transferred to a separate flask and maintained in RPE Propagation Medium (DMEM/F12 (3:1) with 2% B27 and 20 ng/ml each of FGF2 and EGF along with 5 µg/ml of heparin.

To expand the RPE neurosphere populations, the pigmented (RPE) neurospheres are plated onto laminin-coated culture dishes and allowed to adhere in RPE Propagation Medium. Within 24 hours, RPE cells begin to proliferate and expand outward from the plated RPE neurosphere. After 1 week, the RPE neurospheres are gently triturated to remove them from the flask and transferred to another laminin-coated flask to repeat this process (up to 3 times). The remaining skirt of RPE is dissociated enzymatically and replated at a density of 100,000 cells/cm$^2$ and passaged up to 3 times as described for human fetal RPE (Gamm et al, IOVS 49:788 2008, incorporated herein by reference as if set forth herein in its entirety). To promote maturation of RPE, FGF2, EGF and heparin are removed from the RPE Propagation Medium for 1-3 weeks. RPE propagated and differentiated in this manner express numerous RPE markers, including Bestrophin, RPE65, CRALBP, ezrin, Mitf, and ZO-1 among others.

The present invention cultures human pluripotent ESC or iPSC under differentiating conditions to yield major neural retinal cell types and RPE, including populations of RPC and FPC, in convenient sphere forms (neurospheres) that can be easily and inexpensively maintained in culture. The spheres allow recapitulation of more complex 3-D structure of the retina.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

Modeling Early Retinal Development with Human ESC and iPSC

We demonstrate below that cell fate specification and maturation from human ESC of definitive retinal cell populations follows a sequence and time course highly reminiscent of normal retinal development. We also demonstrate that retinal differentiation can be selectively altered by manipulating endogenous developmental signaling pathways. Additionally, we show that an identical cohort of developing retinal cell types can be generated from human iPSC, although variation can occur between lines. Cell populations expressing morphologic features and/or markers of the eye field, RPE, neural retinal progenitors, photoreceptor precursors and photoreceptors were observed in cultures of cells differentiated from human iPSC at time points predicted by results using human ESC.

The findings presented here demonstrate that human ES cells and human iPSC can differentiate in vitro into cells having signature features associated with early eye and retinal development, while following an expected timeline for human retinal development (Barishak, Y., 2001; Finlay, B. L., 2008), thereby meeting the criteria (Keller, G., 2005; Pera, M. F., et al., 2004) for a comprehensive in vitro model system for investigating mechanisms of human retinogenesis involved in retinal specification and differentiation of individual retinal cell types. Furthermore, the highly enriched neurosphere populations described herein can be selectively cultured and isolated from one another and from other cell populations for further differentiation, isolation and use.

Results

Maintenance of Human ESC

Human ESC (H9 line) were expanded on a feeder layer of irradiated MEFs in ESCM containing DMEM/F12 (1:1) (Gibco #11330-065), 20% knockout serum replacement (Gibco #10828-028), 0.1 mM β-mercaptoethanol, 1 mM L-glutamine (Gibco #25030-081), 1% MEM nonessential amino acids (Gibco #11140-050), and 4 ng/mL FGF2 (Invitrogen #13256-029). Cells were passaged every 5-6 days, and morphologically identifiable differentiated cells were mechanically removed at each passage.

Differentiation of Human ESC

Human ESC were Differentiated as Follows:

(1) Making human ESC aggregates: Human ESC were grown on irradiated MEFs to approximately 80% confluence in a 6-well plate. Upon reaching 80% confluence, the human ESC medium was aspirated off and 1 ml of dispase (1 mg/ml, Gibco #17105-041) solution was added to each well. After 5 minutes, the cells were examined for curling of human ESC colony edges, indicative of the colonies beginning to lift off of the plate. If noticeable curling was evident, the dispase solution was aspirated off of the plate and replaced with 1 ml of DMEM/F12 per well. The human ESC colonies were mechanically lifted from the plate by pipetting a few times with a 10 ml pipette. When all colonies were detached, the cells were transferred to a 15 ml conical tube and allowed to settle by gravity. After the aggregates had settled (~5 minutes), the supernatant was aspirated and replaced with 10 ml of Embryoid Body (EB) medium, which contained DMEM/F12 (1:1) (Gibco #11330-065), 20% knockout serum replacement (Gibco #10828-028), 0.1 mM β-mercaptoethanol, 1 mM L-glutamine (Gibco #25030-081) and 1% MEM nonessential amino acids (Gibco #11140-050). The pellet of cells was resuspended by repeated pipetting 2-3 times with a 10 ml pipette, just enough to separate the individual aggregates while minimizing their dissociation. Aggregates were approximately 400 μm in diameter. These aggregates were then transferred to a T25 flask and placed in the incubator. The next day, the aggregates formed floating, sphere-like structures. (If significant attachment of human ESC and/or residual MEF cells was observed, the unattached aggregates were transferred to a new flask.) These cells were fed with fresh EB medium every day for the first 4 days.

(2) Differentiating to anterior neuroepithelial fate: The aggregates were then collected by settling in a 15 ml conical tube and washed once with 10 ml of DMEM/F12. Upon resettlement of the aggregates, the supernatant was removed and the aggregates were re-suspended in 10 ml of Neural Induction Medium (NIM) and transferred to a new T25 flask. NIM included DMEM/F12 (1:1) (Gibco #11330-065), 1% N2 supplement (Gibco #17502-048), 1% MEM nonessential amino acids (Gibco #11140-050), and 2 μg/ml heparin (Sigma #H-3149). Two days later, a 6-well plate was coated with laminin (20 μg/ml diluted in DMEM) and the coated plate was left in the incubator overnight. By this time, aggregates had become brighter and acquired clearly defined edges. The next day, approximately 50 aggregates were plated in each well of a 6 well plate. An additional 2 ml of fresh NIM was added to each well. The cells were then placed in the incubator, making sure the cells were distributed evenly in the plate by gently shaking the plate back and forth as well as side-to-side a few times. Within the first couple of days (by a total of 9 days), most aggregates attached to the laminin-coated surface. These aggregates then flattened somewhat with cells arranged in a monolayer fashion towards the periphery, yet retaining a more 3-dimensional appearance in the center of the aggregate. These cultures were routinely fed with fresh NIM every 2 days. Within a few days, columnar cells developed and formed neural tube-like structures. After a total of 15 days of differentiation (8 days following attachment), it was possible to identify columnar rosette structures within many of these aggregates. A small population of cells that did not display the columnar rosette structures were found on the periphery of these colonies.

(3) Generating retinal progenitor cell (RPC) neurospheres and forebrain progenitor cell (FPC) neurospheres: To allow for retinal differentiation, the central regions of these colonies that possess columnar rosette structures were dislodged from the culture plate using a 1000 μl pipette tip on day 16 of the differentiation, by drawing up some of the medium within the well and squirting the medium directly onto the cell colonies. The columnar rosette cells found in the center of these colonies were denser than those cells in the periphery, so they were easily dislodged by this pipetting technique, leaving the non-rosette cells attached to the plate. We took care not to break up the lifted colonies during this step. Detached colonies were collected in a 15 ml conical tube and spun in a centrifuge at 600 rpm for 1 minute to effectively pellet the detached colonies while leaving most single cells in suspension in the culture medium. The supernatant was then aspirated from the tube and the clusters were re-suspended in 10 ml of Retinal Differentiation Medium (RDM) and transferred to a new T25 flask. RDM included DMEM/F12 (3:1) supplemented with 2% B27. Over the next 24-48 hours, these detached colonies rolled up to form sphere-like clusters of cells (neurospheres), while some of the remaining non-neural cells attached to the flask. Neurospheres were fed every 2-3 days with fresh RDM. Within 3-5 days after detachment of the cells (19th-21st day of the differentiation), neurospheres readily adopted one of two major appearances. Some neurospheres appeared uniform in color and density under bright-field microscopy, typically without defining structural characteristics, but occasionally with a neuroepithelial rosette within them ("non-vesicular" or "non-laminar" morphology). Other neurospheres were distinctly phase-bright, appeared golden in color, with a ring-like, laminar structure on the outside of the neurosphere ("vesicular" or "laminar" morphology). The outer ring of cells appeared to have cells oriented radially outwards from the center. The phase-bright, golden, ring-like neurospheres are comprised of definitive early retinal progenitor cells (RPC). The uniform appearing, non-ring-like neurospheres are comprised of forebrain progenitor cells (FPC).

(4) Isolation of human ESC-derived Retinal Progenitor Cell Neurospheres (RPC neurospheres) and Forebrain Progenitor Neurospheres (FPC neurospheres): To isolate RPC neurospheres from FPC neurospheres, neurosphere populations were separated based on morphological characteristics (see above) at approximately day 20 of differentiation (5 days following detachment), a stage at which there were a minimal number of these clusters sticking to one another and maximal morphological differences. At later time points, the cell aggregates begin to lose their distinguishing characteristics and attach firmly to one another. To collect the neurospheres, the contents of the flask were transferred to a 15 ml conical tube and allowed to settle by gravity (~2-3 minutes). The medium was aspirated and the neurospheres were re-suspended in 5 ml of fresh RDM, and the mixture was then transferred to a 60 mm Petri dish. The Petri dish was placed on a microscope stage and swirled several times to collect the neurospheres within the center of the dish. A P20 pipette was used to gently collect the phase-bright, golden laminar RPC neurospheres into a 15 ml conical tube with 10 ml of RDM inside. This process was repeated to harvest the RPC neurospheres. After the RPC neurospheres were removed, FPC neurospheres were collected according to their morphological characteristics into a separate 15 ml conical tube containing 10 ml RDM. After the FPC neurospheres were isolated, the remaining cells, mixed clusters that were stuck together or those too small to definitively identify, were discarded.

(5) Generating retinal pigment epithelium (RPE): RPE were generated in two ways. In one way, the RPC neurospheres isolated above were cultured in RDM to allow for further maturation. Within an additional 2 weeks of culture of the RPC neurosphere population, a subset of these neurospheres began to develop pigmentation. Within an additional month of culture (2 months total), all cells observed in a subset of neurospheres were pigmented. The pigmentation identified those RPC neurospheres that had adopted a RPE fate (i.e., RPE spheres that express multiple markers of mature RPE such as bestrophin, RPE65, CRALBP, ezrin, Mitf, ZO-1). Additionally, neuroepithelial rosettes (described above) kept attached to the culture surface in RDM after day 15 differentiated over time to RPE. These cells were expanded, as described in Gamm, *Ophthalmol Vis Sci* 2008. Additionally, neuroepithelial rosettes kept attached to the culture surface in RDM after day 15 differentiated over time to RPE.

(6) Further differentiation of FPC: FPC neurospheres differentiated to more mature forebrain neuronal populations within an additional week and expressed such markers as GABA, HuC/D, βIII tubulin and Sox1 as well as Otx2, Sox2 and other forebrain and neural markers.

Eye Field Specification from Human Embryonic Stem Cells

As described above in section (1) and (2) of "Differentiation of human ESC" and as shown in FIG. 1B, human ESC were differentiated as free-floating human ESC aggregates (EBs) and prompted to adhere to the culture dish to permit neuroepithelial rosette formation. After 16 days of differentiation, rosette-containing colonies were mechanically removed and allowed to grow as neurospheres (see section (3), "generating retinal progenitor cell neurospheres and forebrain progenitor cell neurospheres").

RT-PCR experiments were done as follows to check gene expression: Total RNA was isolated from cell cultures from various stages of differentiation using the RNAeasy® kit (Qiagen) and treated with DNAse I. Reverse transcription was performed with the Superscript III RT-PCR kit (Invitrogen). PCR was performed with GoTaq PCR master mix (Promega) and subsequent PCR products were run on 2% agarose gels. For quantitative RT-PCR (qPCR), reactions were performed with Sybr Green Supermix (Applied Biosystems) and the Opticon 2 DNA Engine and Opticon Monitor 2.02 software (MJ Research). Primer sets used are listed in Table 1. All primer sets listed were run for 30 cycles at an annealing temperature of 60° C. unless otherwise noted. Quantitative RT-PCR primers were run for 40 cycles.

TABLE 1

Primers used for RT-PCR.

| Gene amplified | Forward | Reverse | Size (bp) |
|---|---|---|---|
| α-fetoprotein | AGA ACC TGT CAC AAG CTG TG (SEQ ID NO: 1) | GAC AGC AAG CTG AGG ATG TC (SEQ ID NO: 2) | 676 |
| β-Actin (qPCR) | GCG AGA AGA TGA CCC AGA TC (SEQ ID NO: 3) | CCA GTG GTA CGG CCA GAG G (SEQ ID NO: 4) | 103 |
| Bestrophin | ATT TAT AGG CTG GCC CTC ACG GAA (SEQ ID NO: 5) | TGT TCT GCC GGA GTC ATA AAG CCT (SEQ ID NO: 6) | 359 392 |
| Brachyury | ACC CAG TTC ATA GCG GTG AC (SEQ ID NO: 7) | CAA TTG TCA TGG GAT TGC AG (SEQ ID NO: 8) | |
| Chx10 | ATT CAA CGA AGC CCA CTA CCC AGA (SEQ ID NO: 9) | ATC CTT GGC TGA CTT GAG GAT GGA (SEQ ID NO: 10) | 229 |
| Chx10 (qPCR) | GGC GAC ACA GGA CAA TCT TTA (SEQ ID NO: 11) | TTC CGG CAG CTC CGT TTT C (SEQ ID NO: 12) | 122 |
| Crx | TAT TCT GTC AAC GCC TTG GCC CTA (SEQ ID NO: 13) | TGC ATT TAG CCC TCC GGT TCT TGA (SEQ ID NO: 14) | 253 |
| Dkk-1 (qPCR) | AGC ACC TTG GAT GGG TAT TCC AGA (SEQ ID NO: 15) | ACA CAA TCC TGA GGC ACA GTC TGA (SEQ ID NO: 16) | 114 |

TABLE 1-continued

Primers used for RT-PCR.

| Gene amplified | Forward | Reverse | Size (bp) |
|---|---|---|---|
| En-1 | CCC TGG TTT CTC TGG GAC TT (SEQ ID NO: 17) | GCA GTC TGT GGG GTC GTA TT (SEQ ID NO: 18) | 162 |
| GAPDH (23 cycles) | ACC ACA GTC CAT GCC AT CAC (SEQ ID NO: 19) | TCC ACC ACC CTG TTG CTG TA (SEQ ID NO: 20) | 450 |
| HoxB4 (55° C.) | GCA AAG AGC CCG TCG TCT AC (SEQ ID NO: 21) | CGT GTC AGG TAG CGG TTG TA (SEQ ID NO: 22) | 160 |
| Lhx2 | CAA GAT CTC GGA CCG CTA CT (SEQ ID NO: 23) | CCG TGG TCA GCA TCT TGT TA (SEQ ID NO: 24) | 284 |
| Mitf | TTC ACG AGC GTC CTG TAT GCA GAT (SEQ ID NO: 25) | TTG CAA AGC AGG ATC CAT CAA GCC (SEQ ID NO: 26) | 106 |
| Nanog | CAA AGG CAA ACA ACC ACT T (SEQ ID NO: 27) | TCT GCT GGA GGC TGA GGT AT (SEQ ID NO: 28) | 158 |
| Noggin (qPCR) | CCA TCA TTT CCG AGT GCA AGT GCT (SEQ ID NO: 29) | AAG CTA GGT CTC TGT AGC CCA GAA (SEQ ID NO: 30) | 189 |
| Oct4 | CGA GCA ATT TGC CAA GCT CCT GAA (SEQ ID NO: 31) | TTC GGG CAC TGC AGG AAC AAA TTC (SEQ ID NO: 32) | 324 |
| Oct4 (qPCR) | GTG GAG GAA GCT GAC AAC AA (SEQ ID NO: 33) | ATT CTC CAG GTT GCC TCT CA (SEQ ID NO: 34) | 120 |
| Opsin | TAC CTG GAC CAT TGG TAT TGG CGT (SEQ ID NO: 35) | TAA GTC CAG CCC ATG GTT ACG GTT (SEQ ID NO: 36) | 379 |
| Otx2 | CAA CAG CAG AAT GGA GGT CA (SEQ ID NO: 37) | CTG GGT GGA AAG AGA GAA GC TG (SEQ ID NO: 38) | 429 |
| Pax6 | CGG AGT GAA TCA GCT CGG TG (SEQ ID NO: 39) | CCG CTT ATA CTG GGC TAT TTT GC (SEQ ID NO: 40) | 300 (+5a) 258 (-5a) |
| Pax6 (qPCR) | AGT GAA TCA GCT CGG TGG TGT CTT (SEQ ID NO: 41) | TGC AGA ATT CGG GAA ATG TCG CAC (SEQ ID NO: 42) | 120 |
| Pax6(+5a) (qPCR) | CTC GGT GGT GTC TTT GTC AAC (SEQ ID NO: 43) | ACT TTT GCA TCT GCA TGG GTC (SEQ ID NO: 44) | 130 |
| RPE65 | GCC CTC CTG CAC AAG TTT GAC TTT (SEQ ID NO: 45) | AGT TGG TCT CTG TGC AAG CGT AGT (SEQ ID NO: 46) | 259 |
| Rx | GAA TCT CGA AAT CTC AGC CC (SEQ ID NO: 47) | CTT CAC TAA TTT GCT CAG GAC (SEQ ID NO: 48) | 279 |
| Rx (qPCR) | AGC GAA ACT GTC AGA GGA GGA ACA (SEQ ID NO: 49) | TCA TGC AGC TGG TAC GTG GTG AAA (SEQ ID NO: 50) | 81 |
| Six3 (55° C.) | CGA GCA GAA GAC GCA TTG CTT CAA (SEQ ID NO: 51) | CGG CCT TGG CTA TCA TAC ATC ACA (SEQ ID NO: 52) | 394 |
| Six6 | ATT TGG GAC GGC GAA CAG AAG ACA (SEQ ID NO: 53) | ATC CTG GAT GGG CAA CTC AGA TGT (SEQ ID NO: 54) | 385 |

TABLE 1-continued

Primers used for RT-PCR.

| Gene amplified | Forward | Reverse | Size (bp) |
|---|---|---|---|
| SOX1 | CAA TGC GGG GAG GAG AAG TC (SEQ ID NO: 55) | CTC TGG ACC AAA CTG TGG CG (SEQ ID NO: 56) | 464 |
| Sox2 (55° C.) | CCC CCG GCG GCA ATA GCA (SEQ ID NO: 57) | TCG GCG CCG GGG AGA TAC AT (SEQ ID NO: 58) | 448 |
| TII | ATG GCA AAT TCT GTG GCG CTG AAG (SEQ ID NO: 59) | GCG CTG ATT TCC CAA GTG CAT TCT (SEQ ID NO: 60) | 352 |

During this process, human ESC rapidly lost expression of the pluripotency genes Oct4 and Nanog and acquired expression of transcription factors associated with eye field specification (Rx, Six3, Six6, Lhx2, TII and Otx2) as well as neural induction (Pax6, Sox1 and Sox2) (FIG. 1C). In RT-PCR experiments, Pax6 was present as a doublet band at 6 days of differentiation, reflecting the expression of both the Pax6(−5a) and Pax6(+5a) isoforms, also known as Pax6a and Pax6b, respectively. The appropriate staging and lineage of this early cell population was further confirmed by the absence of expression of the retinal progenitor transcription factor Chx10 (also known as Vsx2), the photoreceptor precursor-specific transcription factor Crx and the spinal cord-associated transcription factor HoxB4.

Immunocytochemistry was done as follows to check protein expression: human ESC aggregates or neurospheres were plated onto poly-ornithine- and laminin-coated coverslips overnight to allow for attachment, and then fixed with 4% paraformaldehyde. Cells were then permeabilized in 0.2% Triton X-100 for 10 minutes. For Mitf immunocytochemistry, cells were incubated in ice-cold 90% methanol for 10 minutes as an additional permeabilization step. Immunostaining was performed in 0.1% Triton X-100 and 5% donkey serum using the antibodies listed in Table 2. Labeled cells were visualized with either Alexafluor 488- or Cy3-conjugated secondary antibodies, and nuclei were counterstained with either Hoechst or To-Pro-3 nuclear dyes. Images were obtained from a Nikon TE600 fluorescent microscope equipped with a SPOT camera and software or from z-stacks of cell clusters obtained on a Nikon Cl Laser Scanning Confocal microscope.

Immunocytochemistry showed that nearly all cells within these colonies expressed the anterior neural/eye field transcription factors Otx2 (FIG. 1D) and Lhx2 (FIG. 1E), as well as the definitive neuroepithelial marker Sox1 (FIG. 1F) by day 10 of differentiation.

We demonstrate below that cell fate specification and maturation from human ESC of definitive retinal cell populations follows a sequence and time course highly reminiscent of normal retinal development.

TABLE 2

Primary antibodies used for immunocytochemistry and Western analysis.

| Antibody | Type | Source | Dilution |
|---|---|---|---|
| βIII tubulin | Rabbit polyclonal | Covance | 1:100 |
| Chx10 | Goat polyclonal | Santa Cruz | 1:200 |
| Crx | Mouse monoclonal | Abnova | 1:100 |
| Dkk1 | Mouse monoclonal | Upstate Biotechnology | 1:500 |
| Lhx2 | Goat polyclonal | Santa Cruz | 1:200 |
| Mitf | Mouse monoclonal | Neomarkers | 1:50 |
| Noggin | Mouse Monoclonal | Chemicon | 1:2000 |
| Oct4 | Mouse polyclonal | Santa Cruz | 1:1000 |
| Opsin, red/green | Rabbit polyclonal | Chemicon | 1:5000 |
| Otx2 | Goat polyclonal | R & D Systems | 1:2000 |
| Pax6 | Mouse monoclonal | Developmental Studies Hybridoma Bank | 1:50 |
| Recoverin | Rabbit polyclonal | Chemicon | 1:2000 |
| Rx | Rabbit polyclonal | Abcam | 1:1000 |
| Sox1 | Goat polyclonal | R & D Systems | 1:1000 |
| ZO-1 | Rabbit polyclonal | Zymed | 1:100 |

The gene and protein expression of Pax6 and Rx was examined in further detail, because eye field cells are often characterized by the coexpression of these two transcription factors (Osakada, F., et al., 2008; Mathers, P. H., et al., 2000). RT-PCR and quantitative PCR (qPCR) analysis were done as described above and revealed the onset of expression of both Pax6 and Rx within the first few days of differentiation (FIG. 2A-C), which was closely correlated with loss of Oct4 expression. At the protein level, nearly all H9-derived cells co-expressed both Pax6 and Rx within 10 days of differentiation as determined by immunocytochemistry (FIG. 2D).

FACS analysis was done as follows to quantify the percentage of cells acquiring expression of Pax6 and Rx: Cells were dissociated with either trypsin or Accutase® (Chem icon), washed with a fluorescence-activated cell sorting (FACS) buffer (PBS, 0.1% sodium azide, and 2% donkey serum), and fixed with 0.1% paraformaldehyde for 10 minutes. Cells were then permeabilized with ice-cold 90% methanol for 20 minutes and incubated overnight in primary antibodies at a concentration of 1 µg of antibody per 1 million cells in FACS buffer. Antibody information is found in Table 2. Immunostaining was then completed with either donkey-anti-mouse or donkey-anti-rabbit Alexa 488 secondary antibodies for 2 hours, after which cells were washed with FACS buffer, and then sorted with a Becton Dickinson FACSCaliber. Data retrieved from the sorting was analyzed with CellQuest Pro software (Becton Dickinson).

Cell populations were analyzed by FACS over the first 16 days of differentiation (FIG. 2E-F). The onset of Pax6 and Rx expression was detected by day 6, when approximately 25% of all cells expressed these factors. Expression of Pax6 and Rx surpassed 90% of cells by day 10 of differentiation and increased to greater than 95% by day 16. Conversely, protein expression of Oct4 decreased to an undetectable level by 10 days of differentiation.

The generation of a high percentage of cells with eye field characteristics in the absence of exogenous Wnt and BMP antagonists prompted further investigation into the endogenous expression of Dkk-1 and Noggin in differentiating human ESC cultures. Both genes were upregulated during eye field specification (FIG. 2G) as determined by qPCR.

Furthermore, Western analysis was done as follows to determine expression of Dkk-1 and Noggin: 20 μg protein samples obtained from cell lysates were separated on 4% to 20% gradient Tris-CI gels (Bio-Rad), electroblotted onto PVDF membranes and stained with Ponceau red to confirm transfer. Membranes were blocked with 5% nonfat dry milk and 2.5% BSA in TBST for 1 hour at room temperature followed by consecutive 1 hour incubations at room temperature with primary antibody in TBST+1.5% BSA and HRP-conjugated secondary antibody in TBST+1% nonfat dry milk. Primary antibodies used for Western blot analysis were directed against Noggin and Dkk-1 (see Table 2). Protein bands were visualized by chemiluminescence (ECL Plus® Western Blot Analysis Detection Kit; GE Healthcare, Chalfont St. Giles, UK).

Figures 3A, 3B:
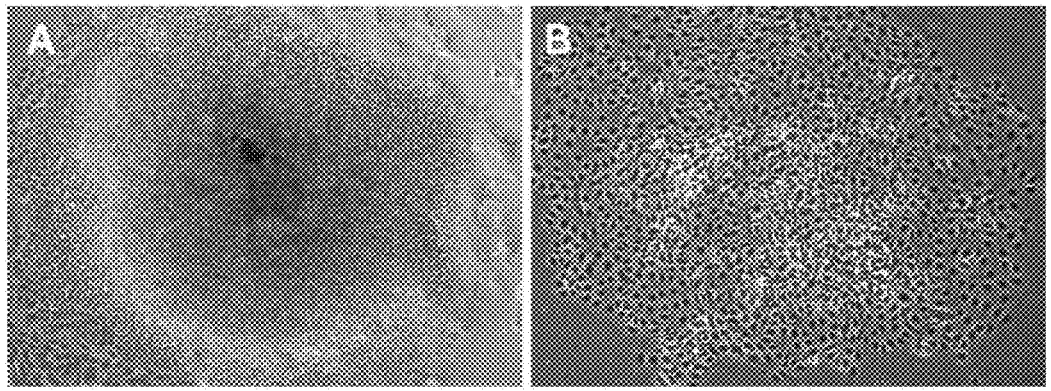
FIGS. 3A-3B show repression of neural and eye field fate specification by BMP4 and Wnt3A. (A) In the absence of exogenous Wnt and BMP antagonists, cells in typical human ESC neuroepithelial colonies at day 10 of differentiation were tightly packed together and individual cells were nearly indistinguishable. (B) When 100 ng/ml BMP4 and Wnt3A were added to cultures at the onset of differentiation, human ESC adopted altered, non-neuroepithelial morphologies by day 10.

Western analysis detected protein expression of Dkk-1 and Noggin at day 10 of differentiation (FIG. 2H). Addition of Wnt3A and BMP4 to cultures over the first 10 days of differentiation abolished both the expression of Pax6 and Rx (FIG. 2I) and the appearance of neuroepithelial colonies (FIG. 3).

Figure 4:
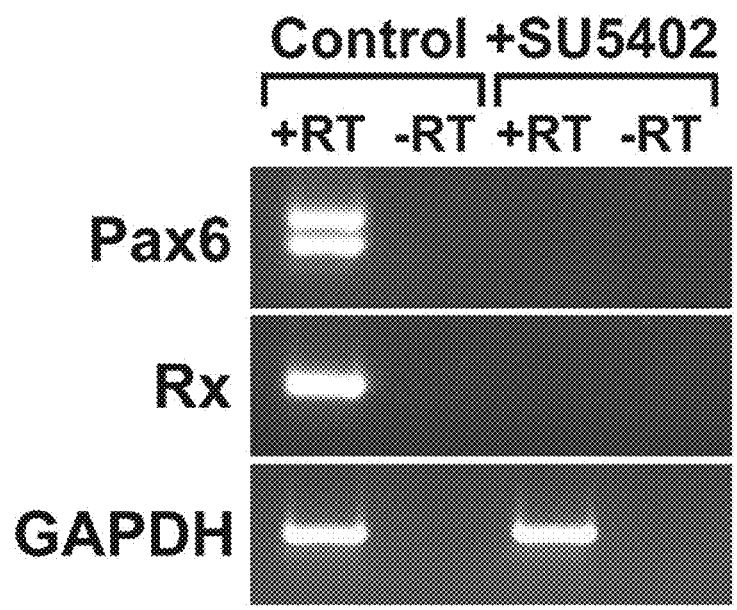
FIG. 4 shows the dependence of eye field specification upon FGF signaling. RT-PCR showing complete loss of Rx and Pax6 gene expression at day 10 of differentiation in the presence of 10 µM SU5402.

Endogenous FGF signaling was also involved in the acquisition of early eye field features, since the addition of the specific FGF receptor inhibitor SU5402 led to a complete loss of both Pax6 and Rx expression at 10 days of differentiation (FIG. 4, tested by RT-PCR).

Acquisition of Optic Vesicle and Optic Cup Cell Phenotypes

Figures 5A, 5N:
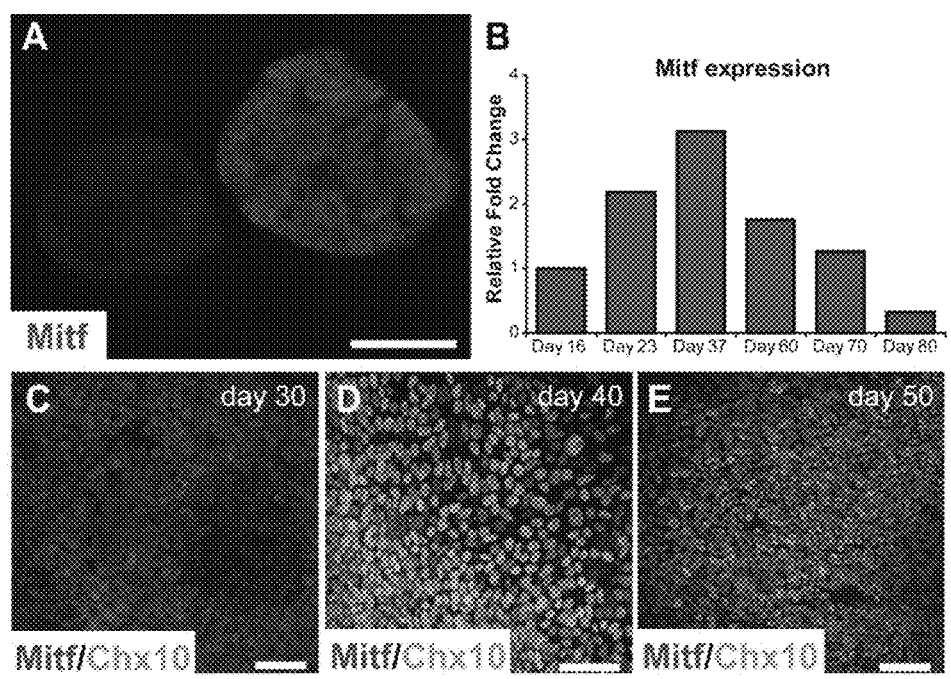
FIGS. 5A-5N show acquisition of optic vesicle and optic cup cell phenotypes. (A) Mitf protein expression in neurospheres after 30 days of differentiation. (B) qPCR analysis of Mitf gene expression over the first 80 days of differentiation. (C-E) Immunocytochemical analyses of the time course of Mitf and Chx10 protein expression in neurospheres at 30 (C), 40 (D) or 50 (E) days of differentiation. (F) qPCR analysis of Chx10 gene expression over the first 80 days of differentiation. (G) Uniform Chx10 expression throughout a subset of neurospheres by day 40. (H-I) Quantification of immunocytochemistry data showing the percentage of Chx10+ spheres (H) and the percentage of Chx10+ cells within those spheres (I) from day 20 to day 50 of differentiation. (J) FACS analysis demonstrating the percentage of all cells expressing Chx10 at day 40. (K) Immunocytochemical analysis showed all Chx10+ cells co-expressed Pax6 at day 40. (L) Rosettes of Chx10-expressing cells expressed the tight junction protein ZO-1 within their core. (M) Rare Chx10+ cells co-expressed βIII tubulin at day 40. (N) qPCR demonstrating the increased expression in Mitf and corresponding decrease in Chx10 in cultures treated with the FGF inhibitor SU5402. qPCR values were expressed as fold change relative to cultures at day 16 (B and F) or day 10 (N) of differentiation. Scale bars equal 500 µm in panels A & G, 50 µm in panels C, D, E, L, & M, and 75 µm in panel K.

When neuroepithelial rosettes corresponding to the eye field stage of retinal development were lifted and grown to neurospheres, nearly uniform expression of Mitf protein was observed within 14.7±2.1% of all spheres by day 30 of differentiation as shown by immunocytochemistry (FIG. 5A). qPCR analysis further demonstrated that gene expression of Mitf increased from day 16 to day 37 of differentiation (FIG. 5B).

Next, the relationship between Mitf and Chx10 protein expression was examined in differentiating neurosphere cultures over time using immunocytochemistry. Chx10 expression was only occasionally observed at day 30 (FIG. 5C). Coexpression of Mitf and Chx10 was prevalent by day 40 (FIG. 5D), followed by mutually exclusive expression of Chx10 and Mitf by day 50 as Mitf expression diminished within Chx10+ neurospheres (FIG. 5E). qPCR analysis confirmed that Chx10 gene expression was delayed relative to Mitf (FIG. 5F). Similar to Mitf, Chx10 protein was eventually detected by immunocytochemistry in nearly all cells of the subset of neurospheres in which it was expressed (FIG. 5G). Quantification of Chx10 protein expression demonstrated that 18.0±3.3% of all neurospheres contained Chx10+ cells by day 40 of differentiation (FIG. 5H), and within these Chx10-expressing neurospheres, greater than 90% of cells expressed Chx10 by day 50 (FIG. 5I). By FACS, 26% of the entire cell culture population expressed Chx10 at day 40 (FIG. 5J). The remaining Chx10-negative neurospheres that were derived from the early eye field cell population maintained an anterior neural identity.

Chx10 expression was associated with a neural cell type that had not yet acquired a mature neuronal phenotype. Among the neurospheres that expressed Chx10, greater than 99% of cells maintained expression of Pax6, which is a requirement of early RPC (Belecky-Adams, T., et al., 1997; Toy, J., et al., 2002) (FIG. 5K). Furthermore, many of the Chx10+ clusters within neurospheres were arranged in rosettes with cells oriented radially away from a core that was positive for the tight junction protein ZO-1 (FIG. 5L), another feature associated with progenitor cell populations (Elkabetz, Y., et al., 2008). When the expression of βIII tubulin, a marker for early post-mitotic neurons, was examined, we found that the Chx10+ rarely co-expressed βIII tubulin, although some clusters that contained Chx10+ cells included a small number of βIII tubulin-positive neurons (FIG. 5M).

Because FGF signaling is suggested to be involved in the specification of the neural retina (Muller, F., et al., 2007), we next examined the effect of SU5402, a potent and specific inhibitor of the FGFR1 receptor, on Mitf and Chx10 gene expression. The addition of SU5402 to human ESC cultures during the optic vesicle stage and optic cup stage of differentiation (days 16-40) resulted in an 11.8-fold increase in Mitf gene expression at day 40, as measured by qPCR (FIG. 5N). By contrast, Chx10 expression was reduced 15.9-fold as a result of this treatment.

Figures 12A, 12B, 12C, 12D, 12E, 12F, 12G, 12H, 12I, 12J, 12K, 12L, 12M:
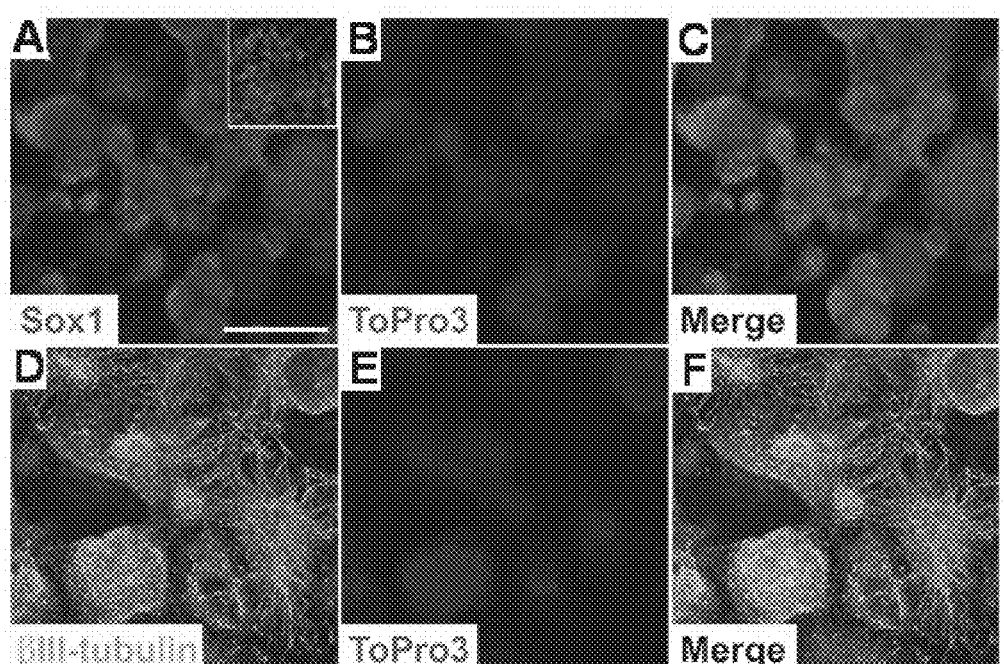
FIGS. 12A-12M characterize FPC neurospheres. Differentiated non-retinal cells retained an anterior neural phenotype. At 40 days of differentiation, all neurospheres expressed the general neural markers Sox1 (A-C) and βIII-tubulin (D-F). (G-I) Many βIII-tubulin+ cells possessed a GABAergic phenotype. (J-L) The forebrain fate of these cells was determined by the widespread expression of Otx2. (M) RT-PCR experiments confirmed that these cells expressed both general and anterior neural markers, but did not express markers of other germ layers, midbrain or spinal cord. Insets demonstrate the nuclear specificity of the signal.

The FPC neurospheres were also characterized, as is shown in FIG. 12. Differentiated non-retinal cells retained an anterior neural phenotype. At 40 days of differentiation, all neurospheres expressed the general neural markers Sox1 (A-C) and βIII-tubulin (D-F). (G-I) Many bIII-tubulin+ cells possessed a GABAergic phenotype. (J-L) The forebrain fate of these cells was determined by the widespread expression of Otx2. (M) RT-PCR experiments confirmed that these cells expressed both general and anterior neural markers, but did not express markers of other germ layers, midbrain or spinal cord. Insets demonstrate the nuclear specificity of the signal.

Retinal Pigment Epithelium (RPE) Specification

Figures 6A, 6B, 6C, 6D:
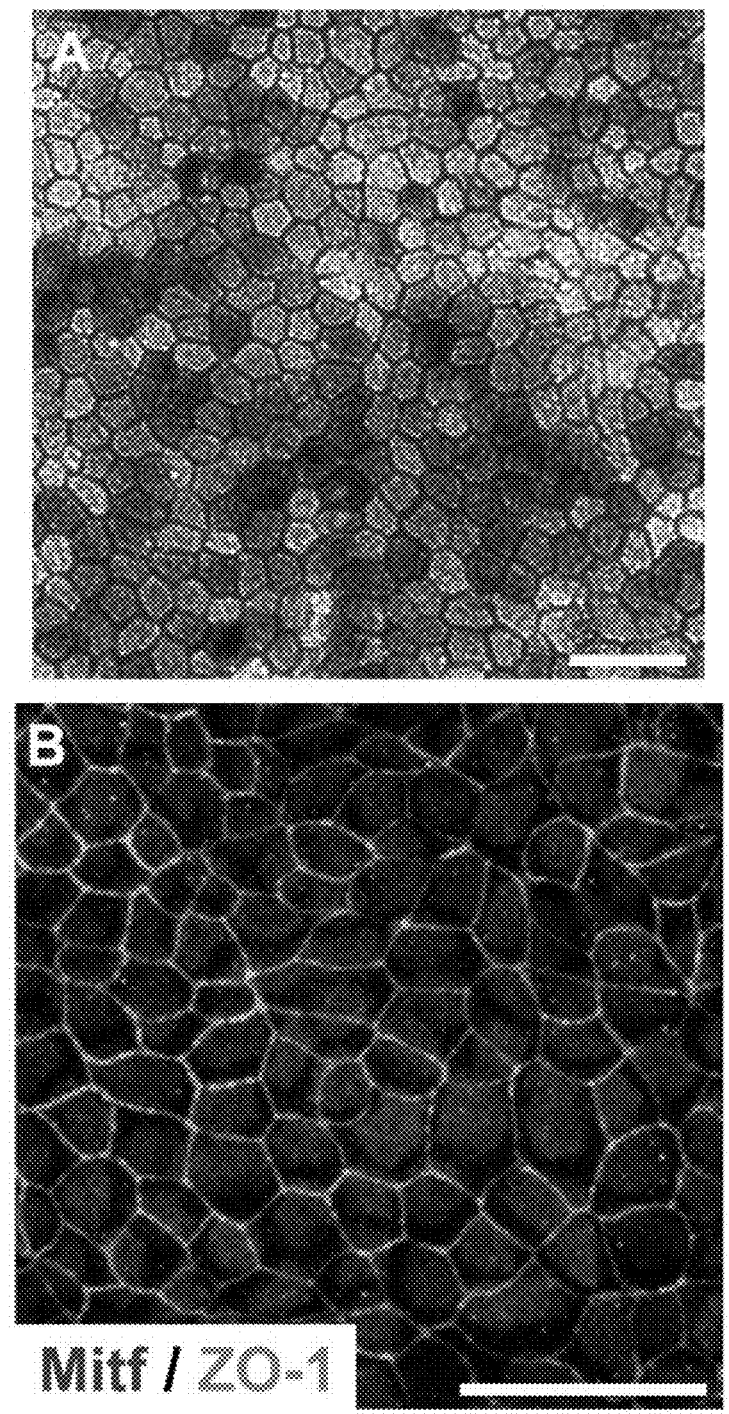
FIGS. 6A-6D show generation of RPE. (A) Photomicrograph of adherent cultures showing pigmented, hexagonal RPE-like cells. (B) Immunostaining revealing expression of Mitf within RPE-like cells, as well as the tight junction protein ZO-1, at day 40. (C) FACS analysis demonstrating the percentage of all adherent cells expressing Mitf and Pax6 at day 40 of differentiation. (D) RT-PCR studies showing expression of genes associated with an RPE fate. Scale bars equal 100 µm.

When neuroepithelial rosettes corresponding to the eye field stage of retinal development were maintained as an adherent culture in RDM as described above, distinct patches of polygonal, pigmented cells were initially observed at approximately day 30 of human ESC differentiation (FIG. 6A). These cells maintained expression of the transcription factor Mitf while also expressing the RPE-associated tight junction protein ZO-1 as shown by immunocytochemistry (FIG. 6B). At day 40 of differentiation, FACS analysis revealed that 25% of all adherent cells expressed Mitf, and 77% of all cells expressed Pax6 (FIG. 6C). RT-PCR analysis demonstrated maintained expression of Pax6 in this cell population over time, as well as the acquisition of more mature RPE-associated markers such as RPE65 and bestrophin (FIG. 6D).

Retinal Cell Types Generated from Human ESC-Derived Retinal Progenitors

After prolonged maintenance of the human ESC-derived retinal progenitor neurospheres, the neurospheres matured toward a photoreceptor phenotype. By a total of 3 months of differentiation, the unpigmented, neural retinal RPC neurospheres produced multiple retinal cell types, predominantly photoreceptor precursors (e.g., Crx+) or photoreceptor-like cells (e.g., opsin+ and recoverin+) as well as retinal ganglion-like cells expressing HuC/D and possessing long βIII tubulin+ processes.

Figures 7A, 7B, 7C, 7D, 7E:
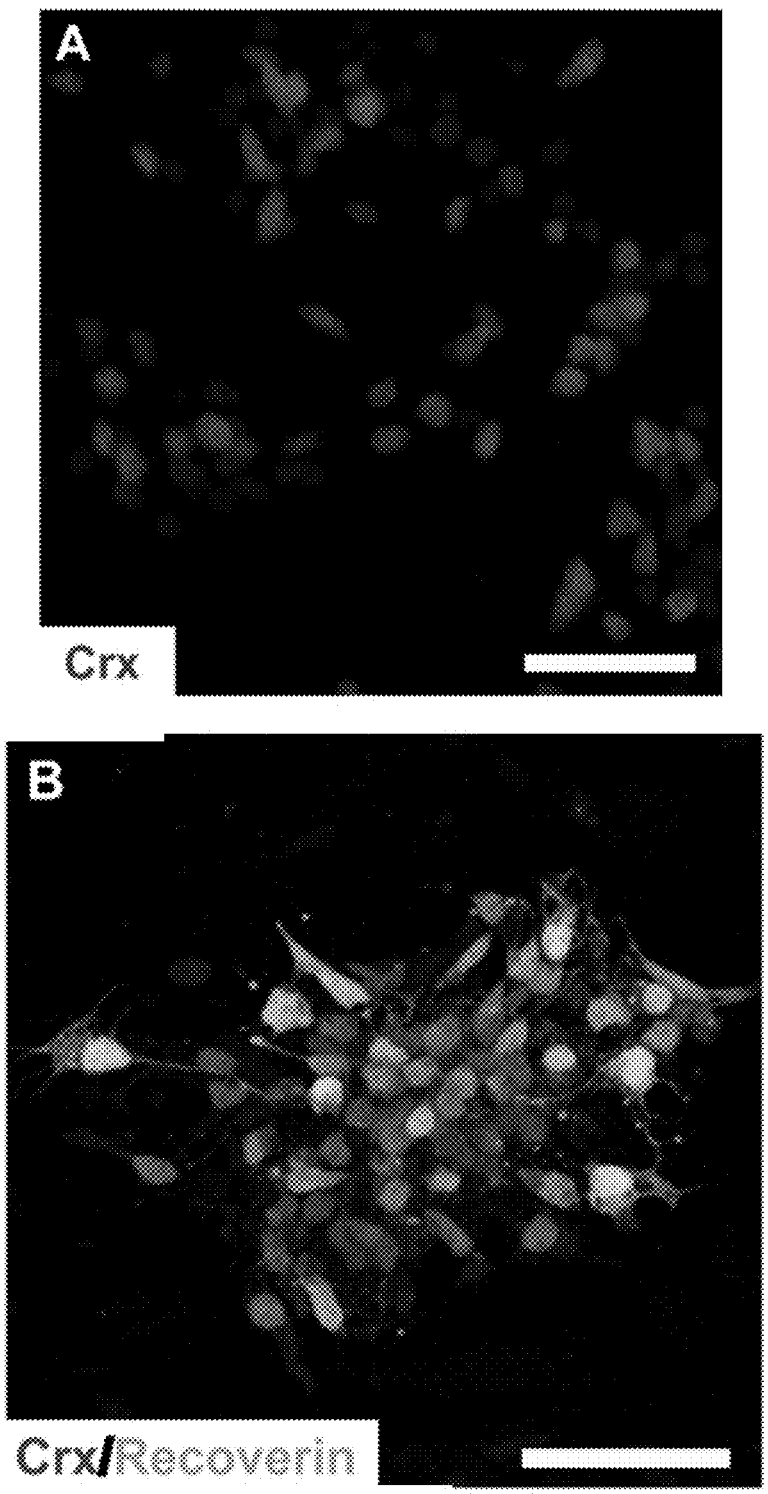
FIGS. 7A-7E show generation of early photoreceptor phenotypes. (A) Immunocytochemical detection of cells expressing the photoreceptor-specific transcription factor Crx at 80 days of differentiation. (B-C) Expression of the photoreceptor-specific protein recoverin (B) and the cone photoreceptor-specific protein red-green opsin (C) among Crx-expressing cells at day 80. (D) RT-PCR analysis demonstrated the stepwise acquisition of a cone photoreceptor fate from an eye field population. (E) Schematic of the timing of retinal lineage marker expression during human ESC differentiation in comparison to normal human retinal development (Barishak, Y., 2001; Finlay, B. L., 2008). Scale bars equal 50 µm

Early Photoreceptor Phenotypes Generated from Human ESC-Derived Retinal Progenitors As shown by immunocytochemistry, by day 80 of differentiation, 19.4±3.1% of all neurospheres contained Crx+ photoreceptor precursors (FIG. 7A). Within these colonies, 63.0±7.6% of all cells expressed Crx. Furthermore, the majority of Crx+ cells expressed the photoreceptor-specific protein recoverin (FIG. 7B) and the cone photoreceptor-specific protein opsin (FIG. 7C).

To analyze the time course and sequential acquisition of neuroretinal- and photoreceptor-associated gene expression, RT-PCR analysis was performed as described above (FIG. 7D). Throughout the differentiation process from day 16 through day 80, Pax6 gene expression was detected. Rx gene expression was also present early in differentiation, followed by the consecutive expression of Chx10, Crx and opsin. Overall, the timing of expression of the gene and protein markers used in this study coincided with that of normal human retinal development (Barishak, Y., 2001; Finlay, B. L., 2008) (FIG. 7E).

Figure 8:
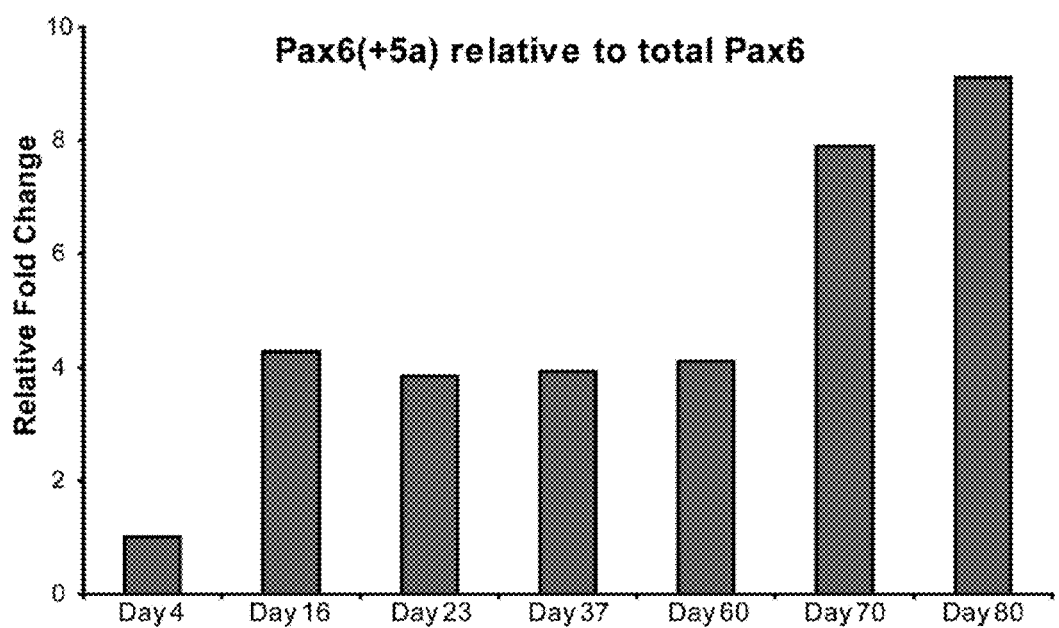
FIG. 8 shows quantitative RT-PCR analysis of Pax6(+5a) expression relative to total Pax6 message in differentiating human ESC-derived neurosphere cultures. Values are expressed as fold change relative to cultures at day 4 of differentiation.

Further evidence of the progression toward a more mature retinal phenotype in these cultures was provided by monitoring Pax6 isoform expression over time by RT-PCR. RT-PCR results from the present study suggested that the Pax6(+5a) isoform became more prevalent during human ESC differentiation (FIGS. 2A and 7D). To verify this observation, qPCR of the Pax6(+5a) isoform relative to total Pax6 expression was performed as described above (FIG. 8). This analysis confirmed the onset of Pax6(+5a) expression between days 4 and 16 of differentiation and demonstrated a relative increase in the expression of this isoform between days 60 and 70, which corresponded to the appearance of photoreceptor-like cells in culture.

Differentiation of Retinal Cell Types from Human iPSC

To determine the potential for stepwise derivation of retinal cell types from human iPSC, we applied the human ESC differentiation protocol described above to four different human iPS cell lines. Consistent with a previous report (Yu, J., et al., 2007), considerable variation was found in the ability of these lines to produce Pax6+ neuroectodermal cells at day 10 of differentiation, with efficiencies ranging from 5% to 56% of the total cell population.

Figure 9:
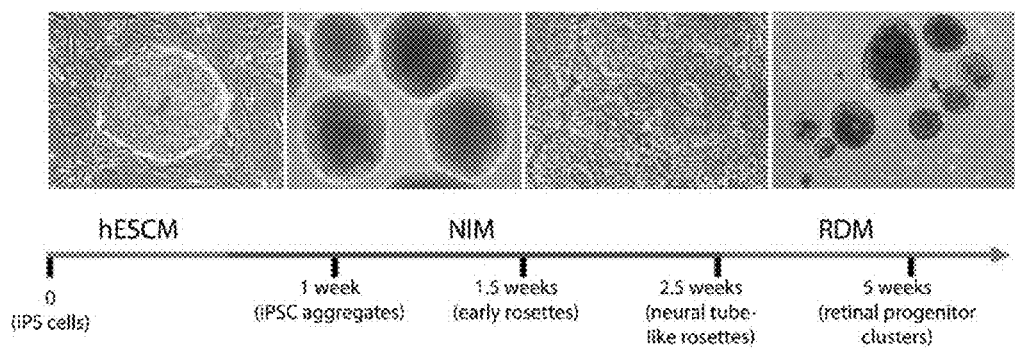
FIG. 9 shows schematic of the differentiation protocol used to generate cells of a retinal lineage from human iPSC.
Figures 10A, 10B, 10C, 10D, 10E, 10F, 10G, 10H, 10I, 10J, 10K:
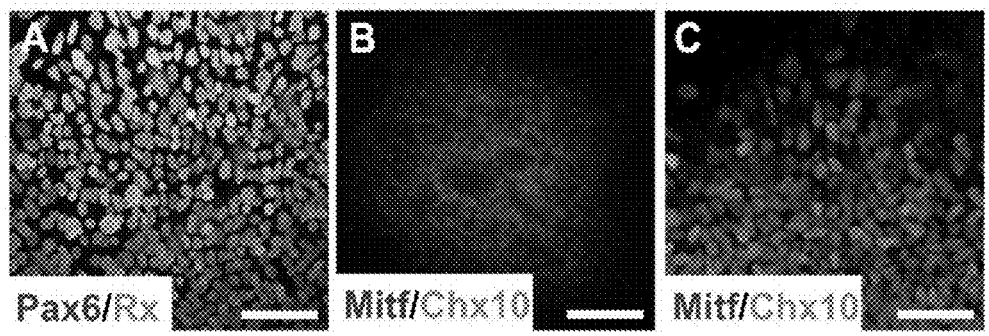
FIGS. 10A-10K show stepwise retinal specification from human iPSC. (A) Various stages of retinal differentiation were observed in IMR90-4 iPSC, beginning with Pax6+/Rx+ eye field cells by day 10. (B-D) Mitf+ and Chx10+ cells, indicative of the optic vesicle and optic cup stages, are evident by day 40. (E) By day 80, clusters were present containing Chx10+ retinal progenitors and Crx+ photoreceptor precursor cells. (F-H) Many Crx-expressing cells were associated with the expression of the photoreceptor-specific protein recoverin (F) and the cone-specific protein red-green opsin (G-H). (I) RT-PCR analysis demonstrating the stepwise expression of retina- and photoreceptor-associated genes in differentiating iPS cell neurospheres over time. (J-K) RPE cells derived from iPSC acquired a typical hexagonal morphology and pigmentation (J) and expressed Mitf and ZO-1 (K). Scale bars equal 50 µm.
Figures 11A, 11B, 11C, 11D:
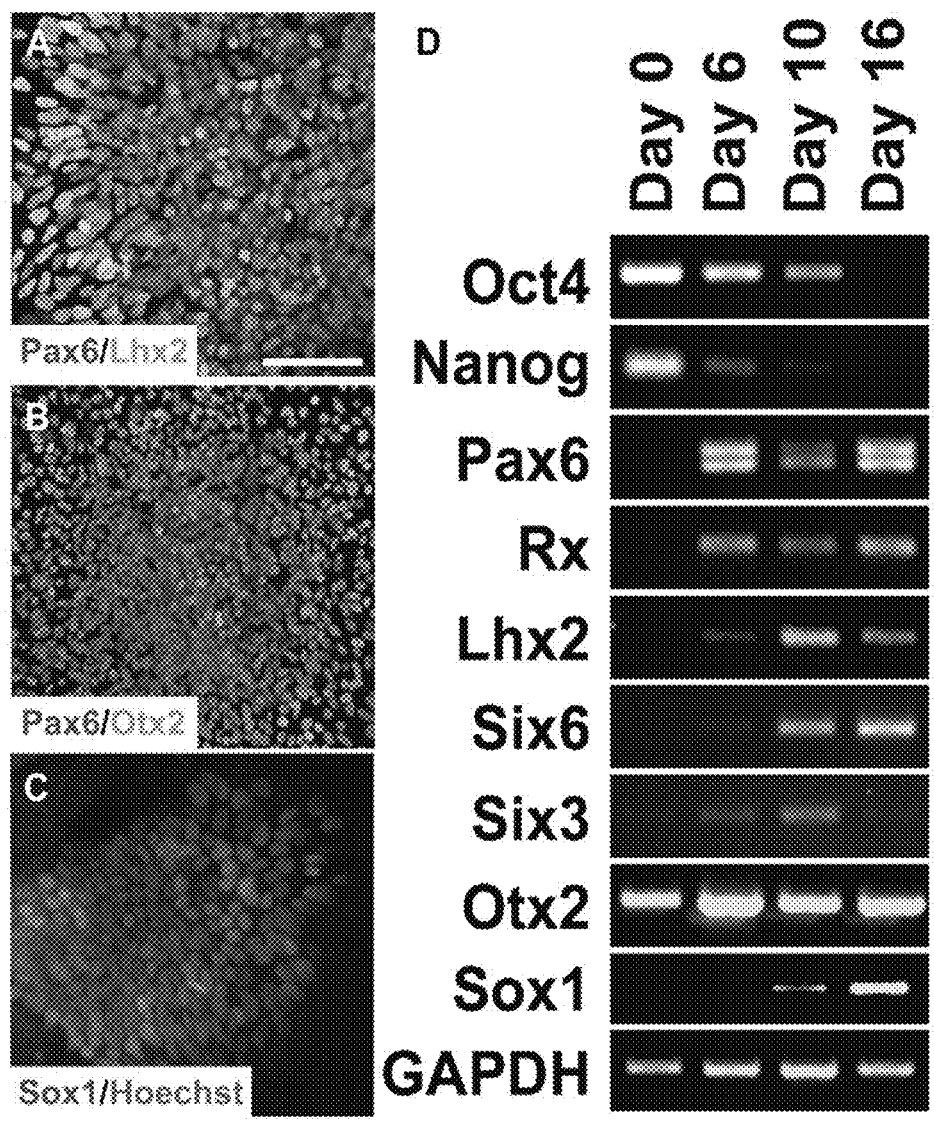
FIGS. 11A-11D show expression of eye field characteristics in differentiating IMR90-4 iPSC. After 10 days of differentiation, iPSC co-expressed Pax6 with eye field transcription factors such as Lhx2 (A), and Otx2 (B). (C) Eye field colonies expressed the definitive neural marker Sox1. (D) RT-PCR over the first 16 days of differentiation demonstrated the expression of a full complement of eye field transcription factors, as well as neuroepithelial markers.

Based on these results, we chose to study the IMR90-4 cell line, one of the highest Pax6-expressing lines (Yu et al., 2007), in greater detail, since Pax6 is necessary for retinal development, although we have obtained, with varying efficiency, RPC and FPC neurospheres from all iPSC lines examined, including lines produced without viral vectors. The cells chosen for extensive study were derived by Yu et al. by reprogramming fetal foreskin IMR-90 (ATCC CCL-186) cells. Upon differentiation, the appearances of the iPS cell colonies, aggregates, neuroepithelial rosettes and RPC and FPC neurospheres were indistinguishable from those of human ESC and the cells differentiated therefrom (FIG. 9). During differentiation, immunocytochemistry revealed early eye field cells co-expressing Pax6 and Rx by day 10 (FIG. 10A). These cells also expressed a full complement of eye field and neuroepithelial transcription factors (FIG. 11). Discrete populations of Mitf+ cells were observed upon further differentiation of eye field colonies as neurospheres (FIG. 10B). Like their human ESC counterparts, many of these iPS cell neurospheres appeared to lose Mitf expression in favor of Chx10 expression (FIG. 10C), yielding neurospheres that were highly enriched for Chx10+ cells (FIG. 10D). Among the total population, 12.9±4.3% of all neurospheres expressed Chx10 at 40 days of differentiation, within which 90.1±1.2% of all cells expressed Chx10. Over time, photoreceptor markers appeared, such as the rod- and cone-specific transcription factor Crx, which was present in 14.4±5.1% of all neurospheres by day 80 (FIG. 10E). Similar to the expression of earlier markers of retinal differentiation, Crx+ cells were common within individual positive neurospheres, constituting 65.5±9.3% of cells. These Crx+ cells frequently expressed the photoreceptor-specific protein recoverin (FIG. 10F) and the cone photoreceptor-specific protein opsin (FIG. 10G-H). RT-PCR analysis confirmed the sequence and timing of gene expression of these markers, along with the early loss of Oct4 expression (FIG. 10I). RPE cells were found within iPS cell cultures as well, with pigmentation first apparent at approximately day 35 of differentiation and typical monolayers arising by day 50 (FIG. 10J). Like human ESC-derived RPE, these cells possessed morphological characteristics of mature RPE and expressed Mitf and ZO-1 (FIG. 10K).

Discussion

We have demonstrated that the production of Pax6+/Rx+ cells is highly efficient, with 95% of all cells co-expressing these essential transcription factors. This efficiency is likely due in part to a relative lack of influence from endogenous BMP and Wnt signaling, since both pathways are known to antagonize neural specification (Glinka, A., et al., 1998; Lamb, T. M., et al., 1993). In support of this theory, increasing expression of BMP and Wnt antagonists (Noggin and Dkk-1, respectively) was observed in human ESC cultures shortly after the onset of differentiation. Early exposure of differentiating human ESC to recombinant BMP4 and Wnt3a eliminated the expression of Pax6 and Rx, as well as the subsequent formation of neuroepithelial rosettes.

The enriched Pax6+/Rx+ cell population derived in this study most closely resembled a primitive stage of human eye field development, which preceded the appearance of committed retinal progenitors, because the majority of the early Pax6+/Rx+ population did not subsequently adopt cellular phenotypes of the optic vesicle or optic cup despite retaining an anterior neural identity.

Our results provide evidence that human ESC proceed through analogous stages of early retinal differentiation, as indicated by the spatiotemporal expression of Mitf and Chx10 in neurospheres. Furthermore, mechanisms governing cell fate choice in the developing retina may also function in differentiating human ESC cultures, as inhibition of endogenous FGF signaling during the optic vesicle and optic cup stages of human ESC differentiation resulted in a profound increase in Mitf gene expression and a corresponding decrease in Chx10 gene expression.

After adopting a retinal fate, individual neurospheres yielded photoreceptor precursors in a time frame predicted by normal human retinogenesis. As with earlier stages of retinal differentiation, this was achieved without adding specific exogenous agents.

Taking into account the entire human ESC population present at the start of the differentiation process, we observed a decrease in targeted cell production with each subsequent stage of retinal differentiation. This observation is consistent with normal retinal development, where early cell types often give rise to multiple distinct progeny of the same lineage. However, there now exist opportunities to introduce exogenous factors for defined time periods to augment production of retinal cell types at specific developmental stages. Such precision is likely to be important, since a single factor can have diverse effects on cellular fate choice depending on the stage of development (Esteve, P., et al., 2006). For example, we observed that early inhibition of endogenous FGF signaling in differentiating human ESC resulted in a loss of eye field specification, whereas later inhibition differentially regulated genes important for the induction of RPE and neural retina progenitors. Manipulation of the culture environment with signaling factors may also alter the time course of retinal cell differentiation from human ESC.

Given the ability of human ESC to mimic normal human retinogenesis, we investigated whether another source of human pluripotent stem cells, iPSC, displayed a similar potential using the same culture method, and confirmed the previous report (Yu et al., 2007) that human iPSC lines differed in their early expression of Pax6. While IMR90-4, one of the highest Pax6-expressing lines, was efficient at producing retinal cell populations, other iPSC lines displayed reduced competency to produce neural and retinal cell types, a phenomenon also observed by Hirami et al. (2009). Therefore, present techniques for deriving iPSC from somatic cells do not always yield uniform lineage competencies between lines.

A detailed knowledge of the stages and time course of retinal differentiation from human ESC and iPSC not only provides an opportunity to study fundamental questions of human retinal development, but may also aid efforts to use pluripotent stem cell derivatives for pharmaceutical testing and retinal repopulation studies. The near absence of contamination from non-neural cell types and the potential to enrich for discrete retinal cell types, including RPC and RPE and FPC further add to the possible clinical and scientific utility of these differentiating cultures. Convenient isolated neurosphere populations of multipotent RPC, RPE and FPC can be produced and supplied for a number of uses. Moreover, the potential for iPSC to generate multiple retinal cell types will aid in the development of in vitro models of human retinal degenerative diseases and stimulate investigation into customized stem cell therapies for patients afflicted by these disorders (Ebert, A. D., et al., 2009; Park, I. H., et al., 2008).

Example 2

Additional Aspects of the Methods Disclosed in Example 1 to Separate Neuroepithelial Lineage Cells by Progenitor Cell Type Introduction Previous studies have demonstrated the ability of hPSCs (human pluripotent stem cells, which include both hESCs and hiPSCs) to differentiate towards the retinal lineage. However, these retinal cells have often been found within a mixed population of cells that have either been unidentified or of a non-retinal lineage. This feature has complicated studies of the cell fate decisions leading to the development of the retina, particularly because many characteristics typically used to identify retinal cell types within the retina are often shared throughout the central nervous system. When these cells are derived from a pluripotent cell source such as hESCs or hiPSCs, the mere expression of these characteristics does not sufficiently identify them as definitively of a retinal nature. Thus, it would be necessary to be able to identify and enrich for multipotent retinal progenitor cells in order to properly study the development of the retina and disorders associated with it.

In this example, we were able to identify and isolate neurosphere populations of cells that were highly enriched for Chx10-positive retinal progenitor cells. With this population of cells, it was possible to study principles of human retinal development, including the sequence and timing of generation of all of the major classes of retinal cell types, as well as mechanisms cell fate determination. In our application of this approach to a hiPSC line derived from a patient with gyrate atrophy, it was possible to study disease progression and provide the proof of principle that hiPSCs can be used as a tool for pharmacological screening for disorders of the retina. These findings are among the first to demonstrate the ability to highly enrich a cell population for a specific progenitor cell population, and serves as the first demonstration of the utility of hiPSCs to serve as a tool for studies of retinal disorders.

Results

Identification, characterization, and separation of optic vesicle-like cells.

Among the earliest stages of retinal development is the establishment of the optic vesicle. Formed as an evagination of the primitive forebrain, the cells of the optic vesicle share many characteristics with the early anterior neuroepithelium, but also have some key differences as well. In Example 1 above, we demonstrated the ability to differentiate hPSCs, including ESCs and hiPSCs, towards a population of cells including both retinal progenitor cells and forebrain progenitor cells. Interestingly, Chx10-positive retinal progenitor cells in these cultures became segregated into individual neurospheres, whereas other neurospheres seemed to be entirely Otx2-positive forebrain progenitor cells.

The ability to identify and isolate the Chx10-positive retinal progenitor neurospheres would allow for numerous experimental possibilities. A highly enriched population of retinal progenitor cells would have implications for cell-based therapy for retinal disorders. Furthermore, such a retinal progenitor cell population would allow for studies of human retinal specification at stages of development that would otherwise be inaccessible. Finally, at their earliest stages of differentiation, the ability to identify and isolate enriched populations of both retinal and forebrain progenitor cells could lead to a better understanding of the mechanisms underlying the decision of a primitive anterior neuroepithelial cell to develop into either a cell of the retina or the forebrain.

Figures 13A, 13B, 13C, 13D, 13E, 13F, 13G, 13H, 13I, 13J:
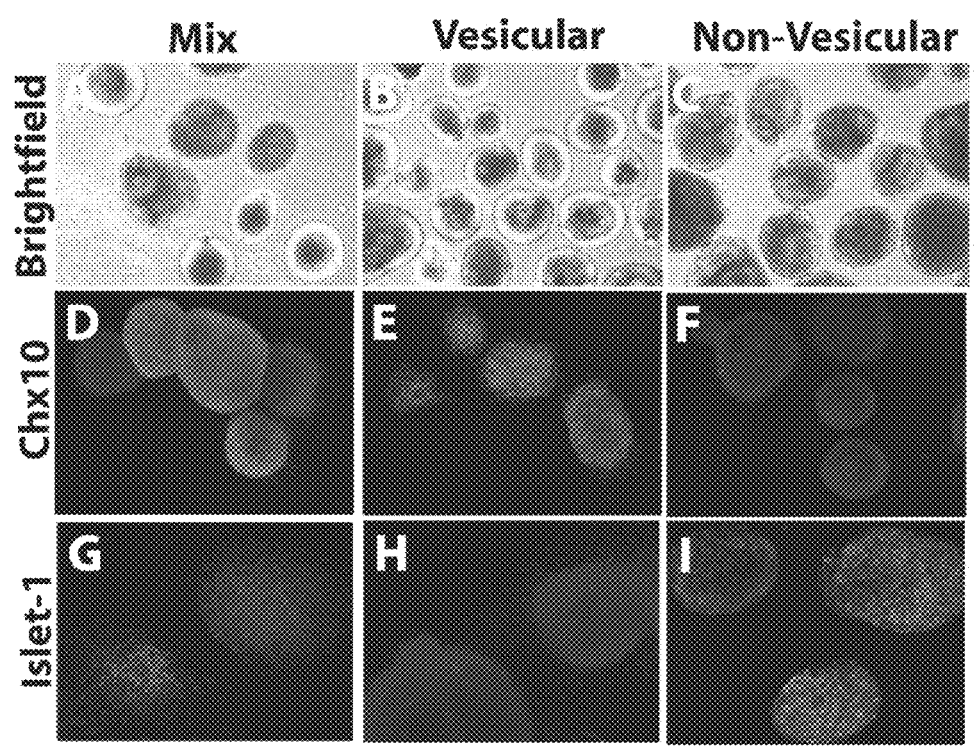
FIGS. 13A-13J show the identification of retinal cells in mixed neurosphere populations using brightfield microscopy (A-C), immunocytochemistry (D-I), and RT-PCR (J). Neurospheres bearing varied morphologies (A) can be separated into two distinct populations of phase-bright vesicular shaped neurospheres with a pseudostratified cellular border (B) and darker, rosette-containing (non-vesicular) neurospheres (C). The definitive retinal progenitor marker Chx10 was identified in a subset of mixed neurospheres (D), and was restricted to only the phase-bright vesicular shaped neurospheres (E) and was absent from the non-vesicular, rosette-containing neurospheres (F). Additionally, the expression of Islet-1 was identified in a subset of mixed neurospheres (G), was not found in the phase-bright vesicular shaped neurospheres (H), but was found to be expressed in the non-vesicular, rosette-containing neurospheres (I). RT-PCR analysis (J) identified a number of transcription factors that were either commonly or differentially expressed between these two populations.

To this end, we first looked for differences within our early neurosphere population derived from hES cells. Following our previous studies (see Example 1), neural-rosette containing clusters of cells were mechanically isolated after 16 days of differentiation and grown in suspension culture as neurospheres. After 20 total days of differentiation, morphological differences became apparent between individual neurospheres (FIG. 13A). When observed using bright field microscopy, some neurospheres appeared phase-bright along the periphery of the cluster and possessed a vesicular or nearly cup-like structure (a "vesicular" or "laminar" morphology). Other clusters appeared more uniform without the phase-bright characteristic along the periphery (a "uniform," "non-vesicular," or "non-laminar" morphology). These latter phenotypes occasionally displayed neural rosette-like structures within them. Based on these morphological criteria, neurospheres could be mechanically isolated into RPC (vesicular) neurospheres (FIG. 13B) and FPC (non-vesicular) neurospheres (FIG. 13C).

Chx10 is known to be the first definitive marker of retinal progenitor cells. Using Chx10 to identify retinal progenitor cells in populations of mixed, vesicular, and non-vesicular neurospheres, immunoreactive cells were abundant (greater than 90%) within the vesicular clusters (FIG. 13E) and completely absent within the non-vesicular clusters (FIG. 13F). Thus, Chx10-positive retinal progenitor cells could be readily identified using morphological features of the cell clusters after 20 days of differentiation. The progenitor cell state of these populations was also further confirmed by the expression of the proliferative marker Ki-67 in both populations (Data not shown). Additionally, when Islet-1 was used to identify forebrain progenitor cells in populations of mixed, vesicular, and non-vesicular neurospheres, immunoreactive cells were abundant within the non-vesicular clusters (FIG. 13I) and completely absent within the vesicular clusters (FIG. 13H). Given the differential expression patterns of Chx10 between the two cell populations, RT-PCR was performed to identify similarities and differences in gene expression (FIG. 13J). Interestingly, the vesicular neurospheres differentially expressed numerous transcription factors known to play a role in early retinal development, including Rax, Lhx2 and Six6, further confirming the identity of these neurospheres as comprising retinal progenitor cells.

Figure 14:
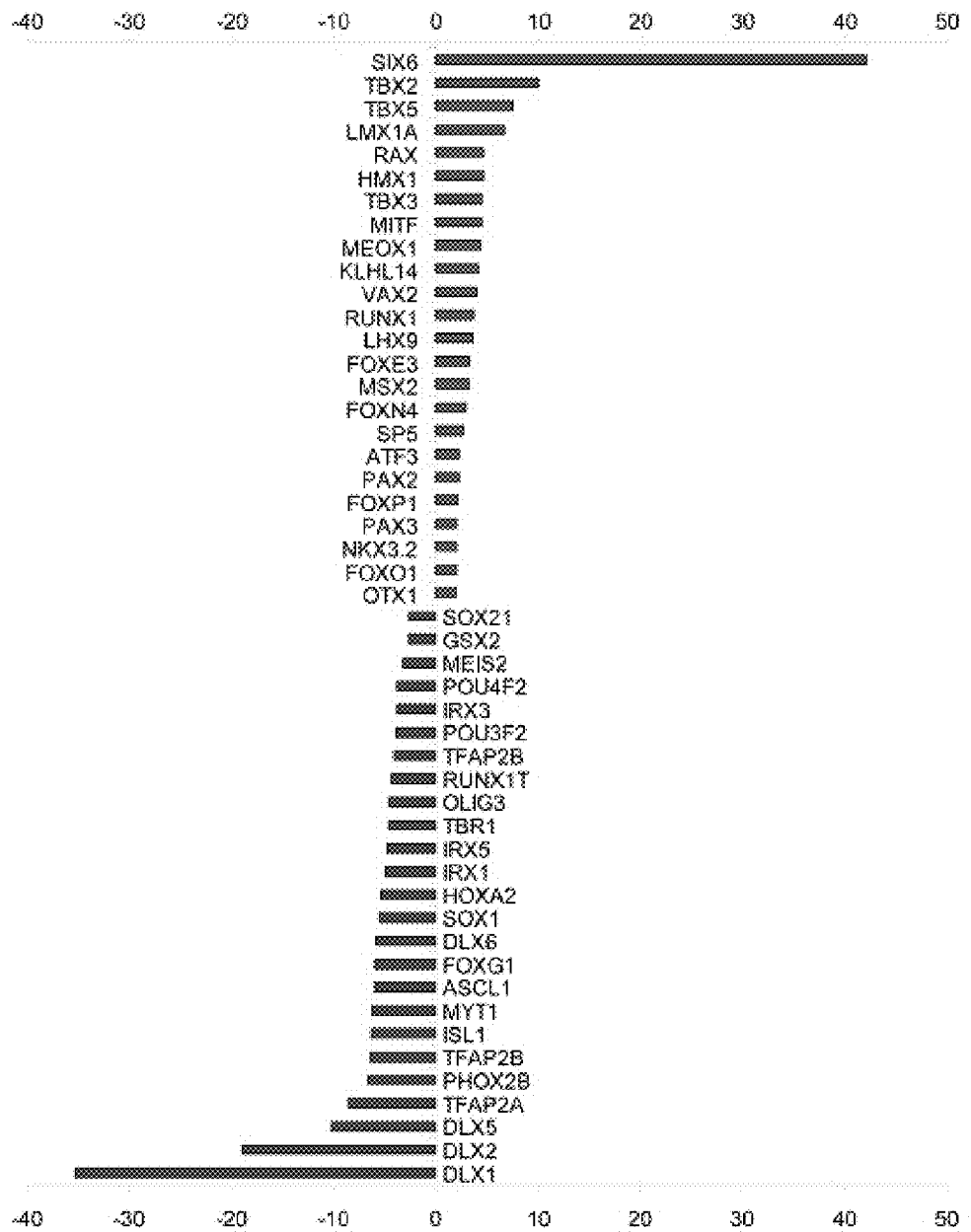
FIG. 14 shows the results of a comparative microarray expression analysis of isolated cultures of vesicular and non-vesicular neurospheres. Numerous transcription factor genes were identified by microarray analysis to be differentially expressed between the two cell populations. Differences are expressed as a fold change in expression for vesicular neurospheres relative to non-vesicular neurospheres.

To further establish the retinal and forebrain identities of the hES cell-derived vesicular and non-vesicular neurospheres, respectively, microarray analysis was performed on the two populations of cells. Vesicular neurospheres differentially expressed many transcription factors associated with retinal development when compared to non-vesicular neurospheres (see FIG. 14). These transcription factors included the eye field transcription factors Six6 and Rax, as well as transcription factors that have been shown to be involved in the optic vesicle stage of retinal development, including Mitf, Tbx2, Tbx5, and Vax2. Conversely, non-vesicular neurospheres differentially expressed numerous transcription factors implicated in the development of anterior neural populations, including Dlx1, Dlx2, Islet-1, and FoxG1.

Human induced pluripotent stem cells (hiPSCs) represent an alternative source of pluripotent stem cells. Derived through the reprogramming of somatic cells with known key transcription factors, hiPSCs have the potential to serve as an autologous source of pluripotent stem cells for transplantation. Furthermore, given the ability to derive hiPSCs from a patient with a known genetic disorder, hiPSCs can serve as an in vitro model for disease progression and drug screening. Before this potential can be realized, however, it is instrumental to determine whether or not hiPSCs respond to inductive cues similarly to their hESC counterparts.

Figures 15A, 15B, 15C, 15D, 15E, 15F, 15G:
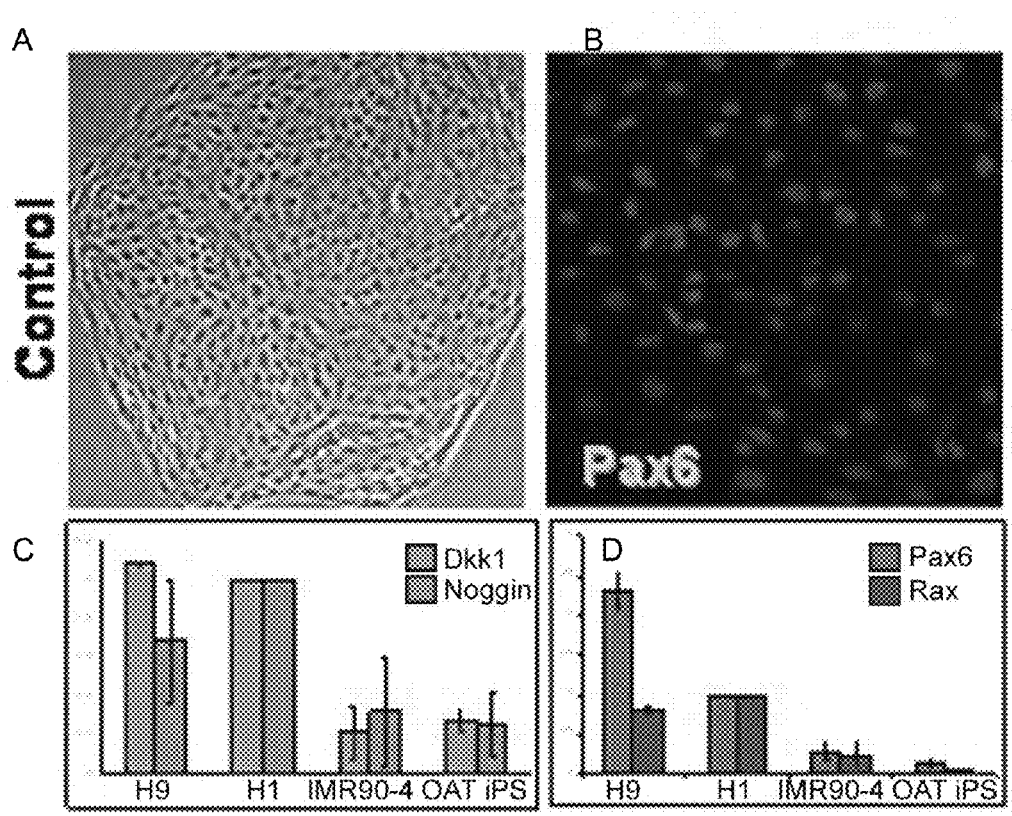
FIGS. 15A-15G show varied neural/retinal specification from hiPSCs (human induced pluripotent stem cells) using bright field microscopy (A and E), immunocytochemistry (B and F), and fluorescence-activated cell sorting (FACS) analysis (G). When subjected to differentiation conditions, hiPSCs commonly adopted a non-neural, epithelial-like morphology (A) that lacked the expression of Pax6 (B). When several lines of hESCs and hiPSCs were compared, IMR90-4 and OAT hiPSCs were found to express lower amounts of Dkk1 and Noggin as compared to H9 and H1 hESCs after 2 days of differentiation (C), which was found to be correlated with lower levels of Pax6 and Rax after 10 days of differentiation (D). When recombinant Dkk1 and Noggin were added to the differentiating cells from 2-4 days of differentiation, a neuroepithelial morphology was identified (E) and the expression of Pax6 was restored (F). Treatment of cells with Dkk1 and Noggin also increased the expression of Chx10 after 20 days of differentiation, as seen using FACS analysis (G).

To this end, several lines of hiPSCs were screened for their ability to produce anterior neural phenotypes upon differentiation. Previous studies have demonstrated the highly efficient derivation of anterior neural phenotypes from several established hESC lines through a nearly default mechanism (see, e.g., Elkabetz, 2008). Following identical induction protocols applied to hESCs, significant variability was found in the ability of hiPSC lines to adopt an anterior neural phenotype, as determined by the expression of Pax6 and Rax, with some lines producing these neural phenotypes poorly and yet others in a rather efficient manner. When we subjected hiPSCs to the differentiation protocol, the cells commonly adopted a non-neural morphology (FIG. 15A) that lacked expression of Pax6 (FIG. 15B).

To establish the underlying mechanisms responsible for this inability to produce neural phenotypes, signaling pathways known to inhibit neural specification were studied. During the development of the nervous system, the BMP and Wnt signaling pathways are known to antagonize neural specification, and endogenous inhibitors of these pathways, Noggin and Dkk-1, have been demonstrated to be conducive to a neural cell fate acquisition. In Example 1, we demonstrated the expression of BMP and Wnt molecules during the neural differentiation of hES cells, along with their respective inhibitors Noggin and Dkk-1. With a focus upon the endogenous expression of Noggin and Dkk-1, several lines of hES and hiPSCs were demonstrated to express these inhibitors at varying levels after 2 days of differentiation (FIG. 15C). This variability was correlated with varying abilities to generate Pax6-positive, Rax-positive anterior neural populations after 10 days of differentiation (FIG. 15D), with those populations more greatly expressing Dkk-1 and Noggin at 2 days of differentiation typically possessing higher levels of Pax6 and Rax after 10 days.

Given the correlation between early expression of Dkk-1 and Noggin and the later acquisition of a Pax6-positive, Rax-positive anterior neural fate, it was likely that the addition of inhibitors of the BMP and Wnt signaling pathways early during the differentiation process might improve the neural specification of those hiPSC lines that had a reduced capacity for such differentiation. To test this hypothesis, inhibitors of BMP signaling (Noggin or Dorsomorphin) and Wnt signaling (Dkk-1 or XAV-939) were added to cultures from days 2 to 4 of differentiation, a timeframe that was shown in Example 1 to be prior to the onset of neural specification based on Pax6 and Rax expression. Following exposure to BMP and Wnt inhibitors, and after a total of 10 days of differentiation, those lines that had previously exhibited a reduced capacity to acquire a neural fate expressed higher levels of Pax6 (FIG. 15F) and Rax. These observations were confirmed through the morphology of hiPSC-derived colonies after 10 days of differentiation, where untreated colonies of cells possessed a flattened appearance and those colonies treated with BMP and Wnt inhibitors possessed a more uniform, epithelial appearance (FIG. 15E). This was further confirmed through immunocytochemistry, where cells treated with BMP and Wnt inhibitors were more likely to express the neural transcription factors Pax6 and Sox1 as well as eye field transcription factors Lhx2 and Six6. After the culture was maintained for a total of 20 days, cells treated with BMP and Wnt inhibitors demonstrated a subset of neurospheres with a morphology similar to the RPC vesicular neurospheres, with these cells largely expressing the retinal progenitor marker Chx10 (FIG. 15G).

Differentiation and Separation of Retina and Forebrain Populations

The neural retina is known to develop in a precise sequence of events and according to a predicted timecourse. Studies of the differentiation of each of the retinal cell types from pluripotent stem cells have been hampered, however, since many of the markers used to identify several cell types within the retina are expressed elsewhere in the central nervous system. As such, one cannot typically identify many retinal cell types unequivocally.

Figures 16A, 16B, 16C, 16D, 16E, 16F, 16G:
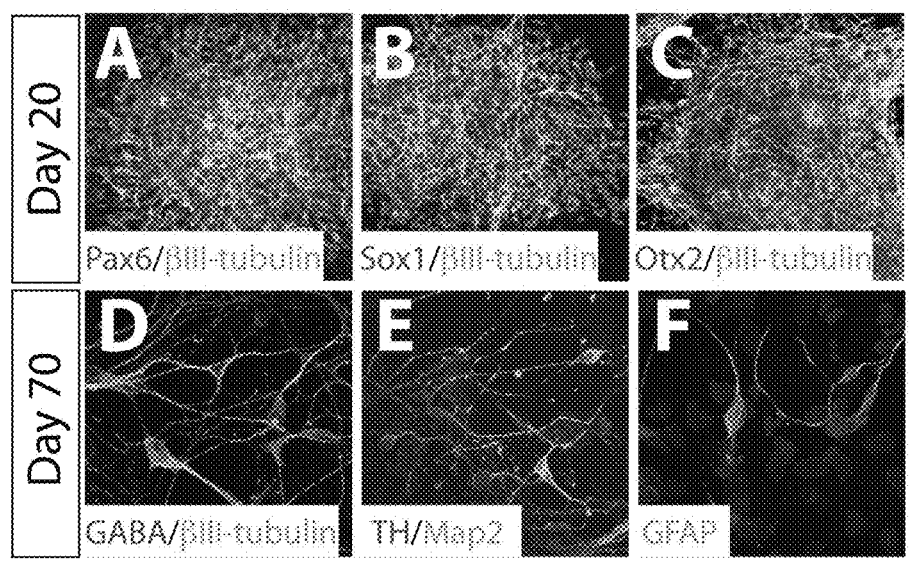
FIGS. 16A-16G show the acquisition of mature anterior neural fate from non-vesicular neurospheres using immunocytochemistry (A-F) and RT-PCR (G). After a total of 20 days of differentiation, non-vesicular neurospheres began to express the neuronal marker βIII-tubulin (A-C), the neural transcription factors Pax6 (A) and Sox1 (B), and the anterior neural marker Otx2 (C). Following a total of 70 days of differentiation, nearly all cells possessed neural morphologies and expressed features of different neural cell types, including GABAergic neurons (D), TH-positive dopaminergic neurons (E), as well as GFAP-positive astrocytes (F). RT-PCR analysis (G) of these cells at 20 and 70 days of differentiation exhibits certain transcription factors whose expression is maintained at both timepoints, as well as some transcription factors that are expressed only at either 20 days or 70 days of differentiation.

In the current study, non-vesicular (FPC) neurospheres maintained an anterior neural fate and were capable of further differentiation to generate varied neural phenotypes. After 20 total days of differentiation, early non-vesicular neurospheres expressed numerous transcription factors associated with a neural fate including Pax6 (FIG. 16A) and Sox1 (FIG. 16B), as well as those of an anterior neural fate such as Otx2 (FIG. 16C). Further maturation of these non-vesicular neurospheres for a total of 70 days yielded varied neural phenotypes, including GABAergic (FIG. 16D) and TH-positive dopaminergic neurons (FIG. 16E), as well as GFAP-positive astrocytes FIG. 16F). RT-PCR analysis (FIG. 16G) of differentiating cells at these timepoints highlights the dynamic nature of this system, where some genes are expressed at both timepoints, others are expressed early but lost in later cultures, while yet other genes are not expressed in earlier cultures but become evident in later cultures.

Figures 17A, 17B, 17C, 17D, 17E, 17F, 17G, 17H, 17I, 17J, 17K, 17L, 17M:
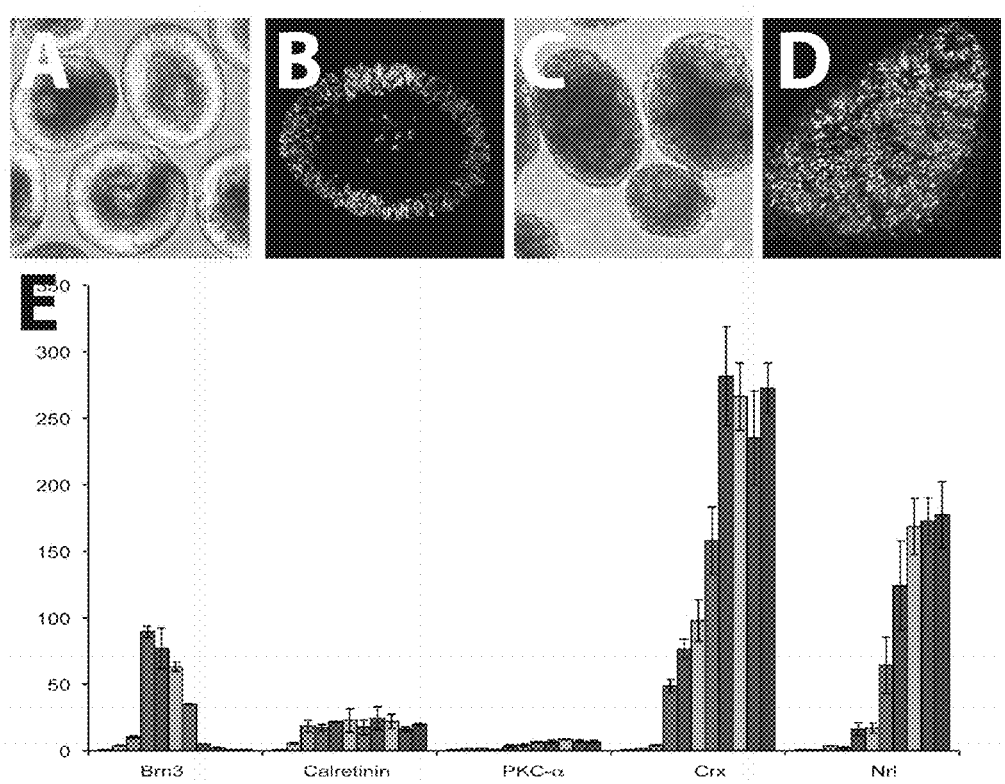
FIGS. 17A-17M show the acquisition of mature retinal identities from vesicular neurospheres using bright field microscopy (A and C), immunocytochemistry (B, D, F-J), RT-PCR (M), and qPCR (E). Vesicular neurospheres at 20 days of differentiation (A) nearly uniformly expressed Chx10, many of which co-expressed Ki67 (B). After a total of 50 days of differentiation, this vesicular morphology tends to be lost (C) but the cells still maintain the expression of Chx10 and Ki67 (D). qPCR analysis of these cells during the differentiation process from day 20 to 120 of differentiation identifies the onset of expression of markers for each of the major retinal cell types in ten day intervals from left to right (E). Those cells known to be born early during normal retinal development were identified as early-born neurons in this system, as identified by orange to red bars, whereas late-born neurons such as PKC-positive bipolar cells and Nrl-positive rod photoreceptors were also found to be born later in this system, as indicated by the green to blue bars. The identity of the different retinal cell types was confirmed by immunocytochemistry with antibodies against cell-type specific proteins, including retinal ganglion cells (F), amacrine and horizontal cells (G), bipolar cells (H), cone precursor cells (I), cone photoreceptor cells (J) including those possessing a morphology similar to photoreceptors found in vivo (K), as well as rod photoreceptor precursors (L). RT-PCR analysis demonstrated the expression of numerous genes associated with the phototransduction cascade (M).

Unlike their non-vesicular neurosphere counterparts, hiPSC-derived vesicular (RPC) neurospheres were demonstrated to possess numerous characteristics associated with early stages of retinal development. These hiPSC-derived vesicular neurospheres (FIG. 17A) are comprised of Chx10-positive, Ki-67-positive retinal progenitor cells nearly exclusively at day 20 of differentiation (FIG. 17B). Further maturation of these cells in vitro demonstrated that although the vesicular morphology tends to be lost (FIG. 17C), many of these cells remained Chx10-positive and Ki-67 positive until at least 50 days of differentiation (FIG. 17D), after which time Chx10 expression began to be lost in favor of more differentiated markers.

Given the high purity of retinal progenitor cells within hiPSC-derived vesicular neurospheres, it was possible to identify differentiated retinal cell types with high degrees of certainty. To accomplish this task, hiPSC-derived vesicular neurospheres were sampled every ten days of differentiation from day 20 until day 120. qPCR analysis (FIG. 17E) demonstrated the onset of expression of individual retinal cell types. Early-born retinal cell types included Crx-positive cone photoreceptors and Brn3-positive retinal ganglion cells, consistent with what is known about retinal development from traditional model systems. Late-born retinal neurons included Nrl-positive rod photoreceptors and PKC-alpha-positive bipolar cells. The existence of each of the major types of retinal neurons was further confirmed with immunocytochemistry against known markers of retinal ganglion cells (FIG. 17F), amacrine and horizontal cells (FIG. 17G), bipolar cells (FIG. 17H), cone precursor cells (FIG. 17I), cone photoreceptor cells (FIG. 17J), including those possessing a morphology similar to photoreceptors found in vivo (FIG. 17K), and rod photoreceptor precursors (FIG. 17L). Quantification of immunocytochemistry results indicated that the predominant cell types generated in this system included Crx-positive cone and Nrl-positive rod photoreceptors as well as Brn3-positive retinal ganglion cells. Furthermore, photoreceptor-like cells generated from hiPSC-derived vesicular neurospheres expressed numerous genes of the phototransduction cascade as determined by RT-PCR (FIG. 17M).

Figures 18A, 18B, 18C, 18D, 18E, 18F:
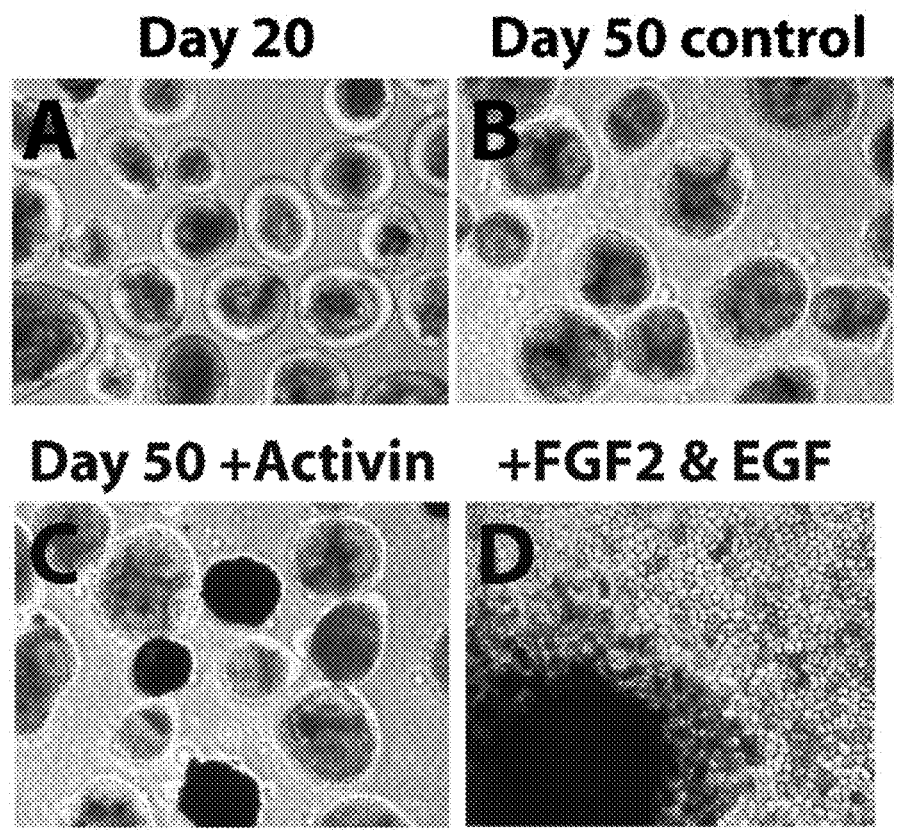
FIGS. 18A-18F show RPE specification from vesicular neurospheres using brightfield microscopy (A-D) and qPCR (E-F). At 20 days of differentiation, retinal vesicular neurospheres can be enriched (A). After a total of 50 days of differentiation, pigmentation characteristic of the RPE was rarely observed (B). After the addition of Activin-A from 20 to 50 days of differentiation, a subset of neurospheres adopted a pigmented, RPE-like morphology (C). These pigmented spheres could be plated onto laminin and expanded in the presence of FGF2 and EGF to form monolayers of RPE (D). When compared to untreated vesicular spheres (leftmost bar in each bar), Activin-A treated spheres (rightmost bar in each pair) expressed higher levels of RPE-associated genes as determined by qPCR (E), whereas neural retinal-associated genes were found to be expressed at lower levels in Activin-A treated neurospheres (rightmost bar in each pair) (F).

These hiPSC-derived vesicular neurospheres were demonstrated to be capable of differentiating into all of the major cell types of the neural retina. If left in a mixed population of vesicular and non-vesicular neurospheres, a subset of vesicular neurospheres became deeply pigmented and appeared to acquire characteristics of the retinal pigment epithelium. However, when these vesicular neurospheres were isolated within the first 3 week of differentiation (FIG. 18A), this ability to differentiate toward an RPE fate was largely absent (FIG. 18B). To better understand the signaling required for the acquisition of an RPE fate, we explored candidate factors known to influence the development of the RPE. If these hiPSC-derived optic vesicle neurospheres truly represent a stage of development analogous to the optic vesicle, they should be able to generate cells of the neural retina and the RPE.

Activin signaling has previously been implicated in this cell fate determination and as such, we sought to determine if Activin could influence these cells to adopt an RPE fate. Activin was added to the vesicular neurosphere cultures upon their isolation from the non-vesicular neurospheres and maintained in the culture until a total of 40 days of differentiation, a timepoint that was demonstrated in Example 1 to be late enough for the acquisition of pigmentation in mixed cultures. In the presence of Activin, a subset of the neurospheres was capable of developing a pigmented phenotype, characteristic of the RPE (FIG. 18C). Based on this feature, these aggregates could be manually isolated to generate highly enriched populations of RPE. When plated onto a laminin-coated substrate and in the presence of the mitogens FGF2 and EGF, these cells were capable of proliferation and outgrowth from the aggregate (FIG. 18D). Subsequent removal of FGF2 and EGF allowed for the maturation of the RPE cells, as demonstrated by the re-establishment of pigmentation and the adoption of a characteristic hexagonal shape. qPCR analysis (FIG. 18E-F) of Activin-treated and untreated optic vesicle populations demonstrated the ability of Activin signaling to influence the relative expression of Mitf and Chx10, transcription factors associated with the development of the RPE and neural retina, respectively. Further maturation of these treated cells confirms that Activin signaling plays a role in the acquisition of an RPE fate at the expense of the neural retina, as Activin-treated cultures expressed RPE-specific genes such as RPE65 at higher levels than the untreated cells, whereas untreated cells expressed higher levels of genes associated with the neural retina including Brn3A (FIG. 18E-F).

Using hiPSC to Model an RPE Disorder

Beyond the ability to study the development of the visual system, the studies presented here also allow for the ability to use hiPSCs to model human disease. Gyrate atrophy is a disorder of the visual system that specifically affects the RPE, with a secondary loss of cells in the neural retina. This disorder is characterized by a defect in the gene encoding for ornithine aminotransferase (OAT). With the goal of developing a unique, human-RPE based system to study this disease and demonstrate its suitability for pharmacological screening, we established lines of hiPSCs from skin fibroblasts derived from a patient with gyrate atrophy. These cells were demonstrated to express all of the pluripotency-associated genes that were examined, and these cells were capable of forming teratomas in a mouse model.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

CITED DOCUMENTS (Each incorporated by reference as if set forth herein in its entirety)

Bailey, T. J., et al. (2004) Regulation of vertebrate eye development by Rx genes. *Int J Dev Biol* 48(8-9):761-770.

Banin, E., et al. (2006) Retinal incorporation and differentiation of neural precursors derived from human embryonic stem cells. *Stem Cells* 24(2):246-257.

Barishak, Y. (2001) *Embryology of the Eye and its Adnexa* (Karger, N.Y.) 2nd Ed.

Belecky-Adams, T., et al. (1997) Pax-6, Prox 1, and Chx10 homeobox gene expression correlates with phenotypic fate of retinal precursor cells. *Invest Ophthalmol Vis Sci* 38(7): 1293-1303.

Bharti, K., et al. (2008) Alternative promoter use in eye development: the complex role and regulation of the transcription factor MITF. *Development* 135(6):1169-1178.

Chen, S., et al. (1997) Crx, a novel Otx-like paired-homeodomain protein, binds to and transactivates photoreceptor cell-specific genes. *Neuron* 19(5):1017-1030.

Chow, R. L., et al. (2001) Early eye development in vertebrates. *Annu Rev Cell Dev Biol* 17:255-296.

Cicero, S. A., et al. (2009) Cells previously identified as retinal stem cells are pigmented ciliary epithelial cells. *PNAS* 106 (16): 6685-6690.

Clegg, D. O., et al. (2009) Derivation of Functional Retinal Pigmented Epithelium from Induced Pluripotent Stem Cells. *Stem Cells* 27 (10): 2427-2434.

Ebert, A. D., et al. (2009) Induced pluripotent stem cells from a spinal muscular atrophy patient. *Nature* 457 (7227):277-280.

Elkabetz, Y., et al. (2008) Human ES cell-derived neural rosettes reveal a functionally distinct early neural stem cell stage. *Genes Dev* 22(2):152-165.

Esteve, P., et al. (2006) Secreted inducers in vertebrate eye development: more functions for old morphogens. *Curr Opin Neurobiol* 16(1):13-19.

Finlay, B. L. (2008) The developing and evolving retina: using time to organize form. *Brain Res* 1192:5-16.

Furukawa, T., et al. (1997) Crx, a novel Otx-like homeobox gene, shows photoreceptor-specific expression and regulates photoreceptor differentiation. *Cell* 91(4):531-541.

Furukawa, T., et al. (1997) Rax, a novel paired-type homeobox gene, shows expression in the anterior neural fold and developing retina. *Proc Natl Acad Sci USA* 94(7):3088-3093.

Gamm, D. M., et al. (2008) A novel serum-free method for culturing human prenatal retinal pigment epithelial cells. *Invest Ophthalmol Vis Sci* 49(2):788-799.

Gamm D. M., Wright L. S, Capowski, E., Kim, H. J., Shearer R. L., Melvan J. N., Schroeder, B. and Svendsen C. N. (2008) Regulation of human retinal neurosphere growth and cell fate potential by retinal pigment epithelia and Mash1. *Stem Cells*, December; 26(12):3182-93.

Glinka, A., et al. (1998) Dickkopf-1 is a member of a new family of secreted proteins and functions in head induction. *Nature* 391(6665):357-362.

Gualdoni, S., et al. (2010) Adult ciliary epithelial cells, previously identified as retinal stem cells with potential for retinal repair, fail to differentiate into new rod photoreceptors. *Stem Cells* 28 (6):1048-1059.

Hirami, Y., et al. (2009) Generation of retinal cells from mouse and human induced pluripotent stem cells. *Neurosci Lett*.

Horsford, D. J., et al. (2005) Chx10 repression of Mitf is required for the maintenance of mammalian neuroretinal identity. *Development* 132(1):177-187.

Hu, B., et al. (2010) Neural differentiation of human induced pluripotent stem cells follows developmental principles but with variable potency. *PNAS* 107 (9):4335-4340.

Keller G (2005) Embryonic stem cell differentiation: emergence of a new era in biology and medicine. *Genes Dev* 19(10):1129-1155.

Klassen, H., et al. (2008) Stem cells in a new light. *Nat Biotechnol* 26(2):187-188.

Klimanskaya, I., et al. (2004) Derivation and comparative assessment of retinal pigment epithelium from human embryonic stem cells using transcriptomics. *Cloning Stem Cells* 6(3):217-245.

Lamba, D. A., et al. (2006) Efficient generation of retinal progenitor cells from human embryonic stem cells. *Proc Natl Acad Sci USA* 103(34):12769-12774.

Lamba, D. A., et al. (2009) Transplantation of human embryonic stem cell-derived photoreceptors restores some visual function in Crx-deficient mice. *Cell Stem Cell* 4:73-79.

Lamb, T. M., et al. (1993) Neural induction by the secreted polypeptide noggin. *Science* 262(5134):713-718.

Li, H., et al. (1997) A single morphogenetic field gives rise to two retina primordia under the influence of the prechordal plate. *Development* 124(3):603-615.

MacLaren, R. E., et al. (2006) Retinal repair by transplantation of photoreceptor precursors. *Nature* 444:203-207.

Mathers, P. H., et al. (2000) Regulation of eye formation by the Rx and Pax6 homeobox genes. *Cell Mol Life Sci* 57(2):186-194.

Muller, F., et al. (2007) Bone morphogenetic proteins specify the retinal pigment epithelium in the chick embryo. *Development* 134(19):3483-3493.

Osakada, F., et al. (2008) Toward the generation of rod and cone photoreceptors from mouse, monkey and human embryonic stem cells. *Nat Biotechnol* 26(2):215-224.

Pankratz, M. T., et al. (2007) Directed neural differentiation of human embryonic stem cells via an obligated primitive anterior stage. *Stem Cells* 25(6):1511-1520.

Park, I. H., et al. (2008) Disease-specific induced pluripotent stem cells. *Cell*134(5):877-886.

Pera, M. F., et al. (2004) Human embryonic stem cells: prospects for development. *Development* 131(22):5515-5525.

Pinson, J., et al. (2005) Regulation of the Pax6: Pax6(5a) mRNA ratio in the developing mammalian brain. *BMC Dev Biol* 5:13.

Rowan, S., et al. (2004) Transdifferentiation of the retina into pigmented cells in ocular retardation mice defines a new function of the homeodomain gene Chx10. *Development* 131(20): 5139-5152.

Takahashi, K., et al. (2007) Induction of pluripotent stem cells from adult human fibroblasts by defined factors. *Cell* 131(5):861-872.

Toy, J., et al. (2002) Effects of homeobox genes on the differentiation of photoreceptor and nonphotoreceptor neurons. *Invest Ophthalmol Vis Sci* 43(11):3522-3529.

Vugler, A., et al. (2008) Elucidating the phenomenon of HESC-derived RPE: anatomy of cell genesis, expansion and retinal transplantation. *Exp Neurol* 214(2):347-361.

Yu, J., et al. (2007) Induced pluripotent stem cell lines derived from human somatic cells. *Science* 318(5858): 1917-1920.

Yu, J., et al. (2009) Human Induced Pluripotent Stem Cells Free of Vector and Transgene Sequences. *Science* 324 (5928):797-801

Zuber, M. E., et al. (2003) Specification of the vertebrate eye by a network of eye field transcription factors. *Development* 130(21):5155-5167.

We claim:

1. A method for generating a cell culture wherein at least 90% of the cells are human retinal pigment epithelium (RPE) cells, comprising
culturing a population of floating human vesicular neurospheres in the presence of Activin until pigmented RPE neurospheres form, wherein the human vesicular neurospheres have a hollow center and an outer ring-like laminar layer comprising human retinal progenitor cells oriented radially outwards relative to the neurosphere center, and wherein the outer ring-like laminar layer appears phase-bright and golden in color when observed using bright-field microscopy,
identifying a plurality of pigmented RPE neurospheres within the population, and
isolating the plurality of pigmented RPE neurospheres from the population and introducing the isolated neurospheres into a culture medium to obtain a cell culture comprising pigmented RPE neurospheres wherein at least 90% of the cells in the cell culture comprising pigmented RPE neurospheres are RPE cells.

2. The method of claim 1, wherein the culturing is serum free.

3. The method of claim 1, wherein the RPE cells comprise the genetic background of a subject having a retinal degenerative disease.

4. The method of claim 1, wherein the culture medium is RPE propagation medium and the method further comprises the step of maintaining the RPE neurospheres in RPE propagation medium to proliferate RPE cells.

5. The method of claim 4, wherein the RPE propagation medium comprises FGF2, EGF, and heparin.

6. A method for generating a cell culture comprising a population of human photoreceptor cells, comprising
culturing a population of human vesicular neurospheres in retinal differentiation medium until Crx+ photoreceptor cells form, wherein the human vesicular neurospheres have a hollow center and an outer ring-like laminar layer comprising human retinal progenitor cells oriented radially outwards relative to the neurosphere center, and wherein the outer ring-like laminar layer appears phase-bright and golden in color when observed using bright-field microscopy.

7. The method of claim 6, wherein the human vesicular neurospheres are cultured for at least 50 days to produce Crx+ photoreceptor cells.

8. The method of claim 7, wherein the human vesicular neurospheres are cultured between 50 days and 3 months to produce Crx+ photoreceptor cells.

9. The method of claim 8, wherein the human vesicular neurospheres are cultured between 50-80 days to produce Crx+ photoreceptor cells.

10. The method of claim 6, wherein the photoreceptor cells also express recoverin.

11. The method of claim 6, wherein the photoreceptor cells also express opsin.

* * * * *

UNITED STATES PATENT AND TRADEMARK OFFICE
CERTIFICATE OF CORRECTION

| | | |
|---|---|---|
| PATENT NO. | : 9,752,119 B2 | Page 1 of 1 |
| APPLICATION NO. | : 15/143141 | |
| DATED | : September 5, 2017 | |
| INVENTOR(S) | : David Matthew Gamm et al. | |

It is certified that error appears in the above-identified patent and that said Letters Patent is hereby corrected as shown below:

In the Specification

Column 1, Lines 20-22 - "This invention was made with government support under MSN116835 awarded by the National Eye Institute. The government has certain rights in the invention." should be --This invention was made with government support under EY015138 awarded by the National Institutes of Health. The government has certain rights in the invention.--.

Signed and Sealed this
Seventh Day of November, 2017

Joseph Matal
*Performing the Functions and Duties of the
Under Secretary of Commerce for Intellectual Property and
Director of the United States Patent and Trademark Office*